(12) United States Patent
Glasbey et al.

(10) Patent No.: US 12,427,215 B2
(45) Date of Patent: Sep. 30, 2025

(54) ENDOSCOPE DISINFECTANT

(71) Applicant: Whiteley Corporation Pty Ltd, North Sydney (AU)

(72) Inventors: Trevor Glasbey, Tanilba Bay (AU); Nicholas Alan Roberts, Woodrising (AU); Gregory Stuart Whiteley, Queenscliff (AU)

(73) Assignee: Whiteley Corporation Pty Ltd, North Sydney (AU)

( * ) Notice: Subject to any disclaimer, the term of this patent is extended or adjusted under 35 U.S.C. 154(b) by 0 days.

(21) Appl. No.: 17/428,334

(22) PCT Filed: Feb. 7, 2020

(86) PCT No.: PCT/AU2020/050101
§ 371 (c)(1),
(2) Date: Aug. 4, 2021

(87) PCT Pub. No.: WO2020/163900
PCT Pub. Date: Aug. 20, 2020

(65) Prior Publication Data
US 2022/0023475 A1 Jan. 27, 2022

(30) Foreign Application Priority Data
Feb. 15, 2019 (AU) .................. 2019900479

(51) Int. Cl.
*A61L 2/18* (2006.01)
*A01N 25/02* (2006.01)
*A01N 25/30* (2006.01)
*A01N 37/16* (2006.01)
*A01N 59/00* (2006.01)

(52) U.S. Cl.
CPC .............. *A61L 2/186* (2013.01); *A01N 25/02* (2013.01); *A01N 25/30* (2013.01); *A01N 37/16* (2013.01); *A01N 59/00* (2013.01); *A61L 2202/17* (2013.01); *A61L 2202/24* (2013.01)

(58) Field of Classification Search
None
See application file for complete search history.

(56) References Cited

U.S. PATENT DOCUMENTS

| | | | | |
|---|---|---|---|---|
| 4,784,799 A * | 11/1988 | Petroff | ............ | C11D 1/92 516/199 |
| 5,093,031 A * | 3/1992 | Login | ............ | A01N 25/14 510/423 |
| 5,202,037 A * | 4/1993 | Lavelle | ............ | C10M 145/36 508/530 |
| 5,545,354 A * | 8/1996 | Ofosu-Asante | ...... | C11D 3/046 510/423 |
| 5,747,439 A * | 5/1998 | Dunn | ............ | C11D 3/0073 510/423 |
| 5,855,217 A * | 1/1999 | John | ............ | B01F 25/3111 134/28 |
| 6,239,089 B1 * | 5/2001 | Cala | ............ | C11D 3/10 510/427 |
| 6,998,376 B1 * | 2/2006 | Tyborski | ............ | C11D 7/06 510/234 |
| 2002/0014611 A1 * | 2/2002 | Taylor | ............ | D06M 13/17 252/8.61 |
| 2003/0129254 A1 * | 7/2003 | Yasuhara | ............ | A61K 31/42 514/557 |
| 2003/0162686 A1 * | 8/2003 | Johansson | ............ | C11D 1/825 510/470 |
| 2006/0241005 A1 * | 10/2006 | Siebert | ............ | C11D 1/94 510/245 |
| 2007/0224135 A1 * | 9/2007 | Liu | ............ | A01N 25/22 424/59 |
| 2008/0039666 A1 * | 2/2008 | Grothe | ............ | C08G 65/2609 568/840 |
| 2009/0005590 A1 * | 1/2009 | DiCosimo | ............ | A01N 59/00 562/2 |
| 2009/0143253 A1 * | 6/2009 | Smith | ............ | B01F 23/232 507/102 |
| 2010/0300044 A1 * | 12/2010 | Man | ............ | C11D 3/2068 516/198 |
| 2012/0204908 A1 * | 8/2012 | Byrne | ............ | C11D 3/2089 134/29 |
| 2013/0171264 A1 * | 7/2013 | Finan | ............ | A01N 25/12 424/615 |
| 2014/0004208 A1 * | 1/2014 | Golden | ............ | A01N 37/16 424/616 |

(Continued)

FOREIGN PATENT DOCUMENTS

| | | | | |
|---|---|---|---|---|
| EP | 1070506 A1 * | 1/2001 | ............ | A61B 1/123 |
| JP | 2009155270 A | 7/2009 | | |

(Continued)

OTHER PUBLICATIONS

Chistov et al. Langmuir 2006 22(10):7528-7542 (Year: 2006).*
Plurafac® LF221 Safety Data Sheet (Year: 2018).*
Fainerman et al. Journal of Colloid and Interface Science 2006 302:40-46 (Year: 2006).*
Fainerman et al. Advances in Colloid and Interface Science 2004 108-109:287-301 (Year: 2004).*
Katara et al. Journal of Patient Safety & Infection Control 2016 4(1):17-21 (Year: 2016).*
Triton® H66 from Dow Chemical Technical Data Sheet (Year: 2024).*

(Continued)

*Primary Examiner* — Melissa S Mercier
*Assistant Examiner* — Caralynne E Helm
(74) *Attorney, Agent, or Firm* — Pryor Cashman LLP

(57) ABSTRACT

A working disinfectant solution comprising peracetic acid and at least one surfactant, prepared by the dilution of either a single-part or two-part concentrate for use in the disinfection or sterilisation of reusable medical devices such as endoscopes. The working solution exhibits rapid wetting characterised by a dynamic surface tension of less than 50 mN/m at 250 ms and 46 mN/m at 500 ms.

13 Claims, 6 Drawing Sheets

(56) References Cited

U.S. PATENT DOCUMENTS

| | | | |
|---|---|---|---|
| 2015/0093425 A1 | 4/2015 | Moore | |
| 2015/0327554 A1* | 11/2015 | Berentsveig | A01N 59/04 424/616 |
| 2016/0221020 A1* | 8/2016 | Rose | B05B 15/00 |
| 2018/0242578 A1 | 8/2018 | Li et al. | |

FOREIGN PATENT DOCUMENTS

| | | | | |
|---|---|---|---|---|
| WO | WO-2006086875 A1 * | 8/2006 | | A61L 2/18 |
| WO | 2018112548 A1 | 6/2018 | | |

OTHER PUBLICATIONS

Dussault "Working with organic peroxides in the academic lab" digitalcommons.unl.edu/cgi/viewcontent.cgi?article=1003&context=chemistryperoxides (Year: 2018).*

Leggett et al. Applied and Environmental Microbiology 2016 82(4): 1035-1039 (Year: 2016).*

Bukton et al. Journal of Pharmaceutical Sciences 1997 86(2): 163-166 (Year: 1997).*

Rapicide® Part A Safety Data Sheet (Year: 2016).*

Rapicide® Part B Safety Data Sheet (Year: 2016).*

Rosen et al. Langmuir 1996 12:4945-4949 (Year: 1996).*

Shah et al. Langmuir 2015 31:13725-13733 (Year: 2015).*

International Search Report in PCT/AU2020/050101 (Apr. 30, 2020).

Written Opinion of the International Searching Authority in PCT/AU2020/050101 (Apr. 30, 2020).

Notice of Acceptance in Australian Patent App. No. 2020222502 (Feb. 8, 2022).

* cited by examiner

ENDOSCOPE DISINFECTANT

BACKGROUND

Reusable medical devices are devices that health care providers can reprocess and reuse on multiple patients. Examples of reusable medical devices include surgical forceps, endoscopes and stethoscopes.

All reusable medical devices can be grouped into one of three categories according to the degree of risk of infection associated with the use of the device:
- Critical devices, such as surgical forceps, come in contact with blood or normally sterile tissue.
- Semi-critical devices, such as endoscopes, come in contact with mucus membranes.
- Non-critical devices, such as stethoscopes, come in contact with unbroken skin.

This classification scheme, devised by Erwin Spaulding, serves as a guide to the reprocessing of reusable medical devices.

Critical medical devices must be reprocessed by sterilisation, ideally by moist heat, or by other means if the device is incompatible with moist heat. Semi-critical medical devices should also be sterilised by moist heat if possible, but at a minimum, by exposure to a high-level disinfectant.

A chemical sterilant is a chemical agent which is used to sterilise critical medical devices. A sterilant kills all microorganisms with the result that the sterility assurance level, i.e. the probability of a single microbial survivor is $\leq 10^{-6}$. A high-level disinfectant (HLD) may be regarded as a subcategory of a sterilant, but exposure time is shorter than required for sterilisation. An HLD kills all microbial pathogens, except large numbers of bacterial endospores when used as recommended by the manufacturer, and is the minimum treatment recommended for the reprocessing of a semi-critical medical device.

A common class of semi-critical medical devices is flexible endoscopes, such as colonoscopes and gastroscopes. Due to their complex construction, and the use of thermolabile materials such as polyurethane sheaths, epoxy coatings, fibre optical cables, photo-optic chips etc, most flexible endoscopes cannot be sterilised by moist heat, and are therefore reprocessed using chemical sterilants or high-level disinfectants.

One popular choice for both chemical sterilisation and high-level disinfection of flexible endoscopes is peracetic acid (PAA).

PAA is normally supplied as an equilibrium mixture of PAA, hydrogen peroxide and acetic acid. PAA is prepared by mixing an aqueous solution of hydrogen peroxide and acetic acid and allowing the material to reach equilibrium. Typically, this reaction is performed uncatalyzed, leaving the reactants to reach equilibrium over 10-14 days, or it may be catalysed by the addition of a strong mineral acid, such as 1% w/w concentrated sulfuric acid.

Commercial grades of PAA are available containing between 5.0 and 5.4% PAA. This concentration of PAA is commonly placed into commerce as it is classified as a Class 5.1 Dangerous Good. Products with a higher concentration of PAA are classified as a Class 5.2 Dangerous Good, and this impacts negatively on transportation costs, as well as storage requirements.

Typically, a 5.0-5.4% w/w PAA equilibrium solution will also contain around 25-28% w/w hydrogen peroxide and 7-10% w/w acetic acid. Often a phosphonic acid chelating agent is added to prevent degradation of the product by trace metal contaminants.

PAA is generally used as a sterilant or HLD for the reprocessing of flexible endoscopes using an Automated Endoscope Reprocessor, or AER. The reprocessing of an endoscope in an AER will typically involve the following steps:
- Placement into an AER
- Pre-wash with water
- Wash phase with a suitable detergent
- Rinse phase using water
- Sterilisation or disinfection
- Multiple rinsing.

The AER will inject the PAA sterilant or disinfectant into the chamber containing the endoscope and dilute it to its working concentration. For high level disinfection, a 5% w/w PAA equilibrium solution is typically diluted to between 1-2% v/v, whereas for sterilisation, it is diluted to between 2-4% v/v. This will give working concentrations of PAA of around 650-1000 ppm for high level disinfection, and 1300-2000 ppm for sterilisation.

Apart from the PAA concentration, the time required to achieve disinfection will also depend on the temperature of the disinfectant or sterilant. For a flexible endoscope, a time of 5 minutes at a temperature between 25° C. and 40° C. is commonly used for high level disinfection, whereas for sterilisation a temperature between 30° C. and 45° C. with a contact time between 7 minutes and 10 minutes is common.

One problem with the use of PAA for endoscope disinfection and sterilisation is corrosion of the endoscope and/or the AER by the acidic, strongly oxidising PAA. This is normally mitigated to some extent by the addition of corrosion inhibitors and pH buffering agents to the diluted PAA solution. Commonly used corrosion inhibitors will include benzotriazole, potassium phosphate, sodium nitrite, sodium nitrate, molybdenum salts, etc.

The corrosion inhibitors and pH buffering agents are typically added as a separate solution to the AER disinfecting chamber as a Part B solution (with the concentrated PAA solution being the Part A solution). This arrangement may be referred to as a 2-part disinfectant or sterilant. Other ingredients may also be added to the Part B solution, for example, wetting agents such as surfactants. The surfactants are added to allow the disinfectant to adequately wet the surface of the endoscope, and to also allow solubilisation of any soil remaining from the cleaning phase.

Typically, nonionic surfactants are used in the Part B solutions as these typically will be low foaming. Examples may include Pluronic 10R5 (see for example WO 2016/100818 to Medivators), Pluronic PE85 and PE64 (see for example US 20030129254 to Saraya). The use of Pluronic surfactants In the Part B formulation is also taught by JP2009155270 to Fujifilm Corporation. It is noted that there are no teachings as to the surface tension of the disinfectant solutions prepared from these formulations.

The use of amine oxide surfactants along with other surfactants has been shown to potentiate biocidal efficacy of PAA based disinfectants, particularly when combined with a phosphate buffer. This has been shown in AU2013359955 (to Saban Ventures). Tested surfactants included cocamidopropylamine oxide. Also tested were other non-ionic surfactants such as Triton X-100 or Tween-80. Cationic surfactants tested included quaternary ammonium compounds such as benzalkonium chloride or hexadecylpyridinium bromide.

The use of amine oxide-based surfactants has also been shown to improve the biocidal efficacy of PAA based disinfectants, particularly when combined with surfactants having the structure shown in formula 1

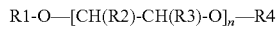    Formula 1 in which R1 represents a linear or branched, saturated or unsaturated aliphatic radical containing from 5 to 31 carbon atoms and preferably from 10 to 16 carbon atoms; R2 represents a hydrogen atom, a methyl radical or an ethyl radical, R3 represents a hydrogen atom, a methyl radical or an ethyl radical, it being understood that at least one of the two radicals R2 or R3 represents a hydrogen atom, R4 represents a hydrogen atom or a linear or branched alkyl radical containing from 1 to 4 carbon atoms, or a benzyl radical, and n represents a number between 1 and 50, and preferably n is less than 20 (see U.S. Pat. Nos. 6,168,808, 6,444,230, and FR2796285, all to Seppic).

One suggestion into the mechanism at play in the improvement of biocidal efficacy of PAA in the presence of surfactants is the improved wetting of the disinfectant in the presence of a surfactant system. For example, EP0971584 (again to Seppic) suggests that a PAA based disinfectant, formulated with an amine oxide based surfactant, particularly in the presence of a surfactant with a structure as shown in formula 1 can show good wetting characteristics on dilution, with static surface tensions of the order of 26.5-31.0 mN/m, when measured using the Wilhelmy plate method.

Interestingly, reproducing these formulations and measuring their surface tensions via the maximum bubble pressure method demonstrate that the examples of EP0971584 show that these formulations are slow wetting, with the surface tensions at a surface age of 15000 ms significantly higher than the static values reported in the '584 document (see Example 9 and FIG. 6).

The discussion of documents, acts, materials, devices, articles and the like, is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

According to a first embodiment of the invention, there is provided a working disinfectant solution for the sterilisation or disinfection of a medical device comprising an aqueous dilution of a disinfectant concentrate comprising: (a) peracetic acid and (b) at least one surfactant, wherein said working disinfectant solution exhibits a dynamic surface tension less than about 50 mN/m at a surface age of 250 ms, and less than about 46 mN/m at a surface age of 500 ms, when measured by the Maximum Bubble Pressure method at 20-25° C.

According to a second embodiment of the invention there is provided a working disinfectant solution of the first embodiment wherein said working disinfectant solution exhibits a dynamic surface tension less than about 42.5 mN/m at a surface age of 250 ms, and less than about 41.0 mN/m at a surface age of 500 ms at 20-25° C., when measured by the Maximum Bubble Pressure method.

According to a third embodiment of the invention there is provided a working disinfectant solution of the second embodiment wherein the working disinfectant solution also exhibits a dynamic surface tension less than about 40 mN/m at a surface age of 5000 ms, when measured by the Maximum Bubble Pressure method.

According to a fourth embodiment of the invention there is provided a working disinfectant solution of any one of the first, second or third embodiments wherein the disinfectant concentrate is provided as a single-part disinfectant concentrate.

According to a fifth embodiment of the invention there is provided a working disinfectant solution of any one of the first, second or third embodiments wherein the disinfectant concentrate is provided as a two-part disinfectant concentrate having a first part and a second part.

According to a sixth embodiment of the invention there is provided a method of disinfecting or sterilizing a medical device, which method comprises contacting said medical device with a working disinfectant solution comprising an aqueous dilution of a disinfectant concentrate comprising (a) peracetic acid and (b) at least one surfactant, wherein said working disinfectant solution exhibits a dynamic surface tension less than about 50 mN/m at a surface age of 250 ms, and less than about 46 mN/m at a surface age of 500 ms when measured by the Maximum Bubble Pressure method at 20-25° C.

According to a seventh embodiment of the invention there is provided a method of disinfecting or sterilizing a medical device, which method comprises contacting said medical device with a working disinfectant solution according to any one of the first to fifth embodiments.

Throughout the description and claims of the specification, the word "comprise" and variations of the word, such as "comprising" and "comprises", is not intended to exclude other additives, components, integers or steps.

DETAILED DESCRIPTION OF THE INVENTION

Figure 1:
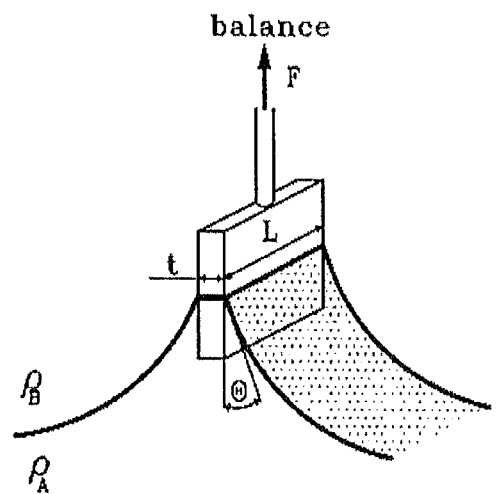
FIG. 1 shows a Wilhelmy Plate apparatus.

Described herein are PAA based disinfectant compositions intended for use in the high-level disinfection and/or sterilisation of complex reusable thermolabile medical devices such as flexible endoscopes. The compositions described are typically produced as concentrates, and then diluted to a preferred working concentration at the point of use. The diluted disinfectant composition is referred to herein as the working disinfectant solution.

Preferably, the working disinfectant solutions of the invention are used in automated washer disinfectors, more preferably automated washer disinfectors intended for the reprocessing of, for example, flexible endoscopes.

The working disinfectant solution of the invention is formed by the dilution of a disinfectant concentrate.

In one embodiment, the disinfectant concentrate is comprised of two parts. The first part is preferably a PAA concentrate, and the second part is preferably a corrosion inhibitor concentrate containing at least one surfactant. The first part (referred to as Part A) comprises an equilibrium solution of PAA, hydrogen peroxide and acetic acid, preferably in combination with a stabiliser and optionally a small quantity of a strong mineral acid. The second part (referred to as Part B) preferably comprises at least one corrosion inhibitor, at least one surfactant, and may optionally contain other ingredients such as hydrotropes, pH adjusting agents, indicators, colourants, chelating agents etc. The working disinfectant solution is formed by mixing Part A and Part B and diluting with water to give the required concentration of PAA.

Preferably Part A will be an equilibrium solution containing between about 0.1% w/w PAA and about 20% w/w PAA. More preferably, Part A will comprise between about 1% w/w PAA and about 15% PAA. Most preferably, Part A will comprise between about 4% w/w and about 6% w/w PAA.

It is noted that commercial equilibrium solutions of PAA (such as Proxitane) will contain stabilisers (often proprietary by nature). These commercial products may also contain small quantities (typically <1%) mineral acids (particularly if manufactured in cold climates).

The second part (hereafter referred to as Part B) comprises an aqueous solution of at least one surfactant and preferably at least one corrosion inhibitor and/or at least one pH modifying agent.

The working disinfectant solution of the invention is thus produced by combining portions of the Part A and Part B solutions with water to produce an aqueous based disinfectant working solution.

Preferably the ratios of Part A and Part B are between about 1:10 to about 10:1 by volume. More preferably, the ratios of Part A and Part B are between about 1:5 to about 5:1 by volume. Most preferably the ratios of Part A and Part B are about 1:1 by volume.

The working disinfectant solution will preferably comprise between about 0.1% v/v and about 10% v/v of Part A and between about 0.1% v/v and about 10% v/v of Part B. More preferably the working disinfectant solution will comprise between about 0.5% v/v and about 5% v/v of Part A and between about 0.5% v/v and about 5% v/v of Part B for high level disinfection and between about 1.0% v/v and about 10% v/v of Part A and between about 1.0% v/v and about 10% v/v of Part B for sterilisation.

The working disinfectant solution exhibits a dynamic surface tension less than about 50 mN/m at a surface age of 250 ms, and less than about 46 mN/m at a surface age of 500 ms at 20-25° C. when measured by the Maximum Bubble Pressure method.

In a preferred embodiment, the working disinfectant solution exhibits a dynamic surface tension less than about 42.5 mN/m, at a surface age of 250 ms, and less than about 41 mN/m at a surface age of 500 ms at 20-25° C. when measured by the Maximum Bubble Pressure method.

In another preferred embodiment the working disinfectant solution exhibits a dynamic surface tension less than about 42.5 mN/m at a surface age of 250 ms, less than about 41 mN/m at a surface age of 500 ms at 20-25° C. and less than about 40 mN/m at a surface age of 5000 nm, when measured by the Maximum Bubble Pressure method.

In another embodiment of the invention, the disinfectant concentrate is provided as a single-part disinfectant composition comprising an equilibrium solution of at least PAA, hydrogen peroxide and acetic acid and at least one surfactant, preferably in combination with a stabiliser. Optionally, the single-part disinfectant concentrate may also comprise at least one corrosion inhibitor, and other ingredients such as hydrotropes, pH adjusting agents, indicators, colourants, chelating agents etc. In use, the single-part disinfectant concentrate is diluted, preferably with water.

The diluted single-part disinfectant concentrate is the working disinfectant solution which exhibits a dynamic surface tension less than about 50 mN/m at a surface age of 250 ms, and less than about 46 mN/m at a surface age of 500 ms at 20-25° C. when measured by the Maximum Bubble Pressure method.

In a preferred embodiment, this diluted single-part disinfectant concentrate forming the working disinfectant solution of the invention exhibits a dynamic surface tension less than about 42.5 mN/m, at a surface age of 250 ms, and less than about 41 mN/m at a surface age of 500 ms at 20-25° C. when measured by the Maximum Bubble Pressure method.

In another preferred embodiment, the diluted single-part disinfectant concentrate forming the working disinfectant solution exhibits a dynamic surface tension less than about 42.5 mN/m, at a surface age of 250 ms, and less than about 41.0 mN/m at a surface age of 500 ms at 20-25° C., and less than about 40.0 mN/m at a surface age of 5000 nm when measured by the Maximum Bubble Pressure method.

Without wishing to be bound by theory, it is believed that the improved rapid wetting provided by the low surface tension at a low surface age allows for the more rapid disinfection of endoscopes within an AER, particularly those employing dynamic cleaning processes such as spray arms etc.

The improved performance of the disinfectant resulting from the rapid wetting of the inventive working disinfectant solution will provide for a more rapid achievement of at least a 6 $\log_{10}$ reduction in both bacteria and spores compared to a prior art PAA based disinfectant solution when tested under the same conditions of PAA concentration and temperature.

Alternatively, or in addition, the inventive working disinfectant solution will provide for the achievement of at least a 6 $\log_{10}$ reduction in both bacteria and spores in the same timeframe as a prior art PAA based disinfectant solution when tested at a lower PAA concentration. The lower concentration will provide for a less corrosive disinfectant solution, but with the equivalent biocidal performance.

Much of the prior art describes both single-part and two-part PAA-based disinfectants containing surfactants, wherein the presence of the surfactant can lead to an increase in the biocidal efficacy of the PAA based disinfectant.

As discussed previously, it has been suggested that the presence of the surfactant leads to better wetting of surfaces by the disinfectant, thus leading to improved disinfection efficacy. EP0971584 describes the likely improved wetting in terms of the lowered surface tension of the disinfectant leading to lower contact angles of the solution on hydrophobic surfaces such as Parafilm. The '584 document however characterised the static surface tensions of the solutions using the Wilhelmy plate method (see Table 1). Dynamic surface tension data was not reported in the '584 document.

TABLE 1

Static surface tensions reported in EP0971584

| EP0971584 | dilution | Static surface tension (mN/m) |
|---|---|---|
| Composition 1 | 80x | ~30 |
| Composition 2 | 40x | ~30 |
| Composition 3 | 40x | ~30.5 |
| Composition 4 | 40x | ~26.5 |
| Composition 5 | 40x | ~31 |

Figure 3:
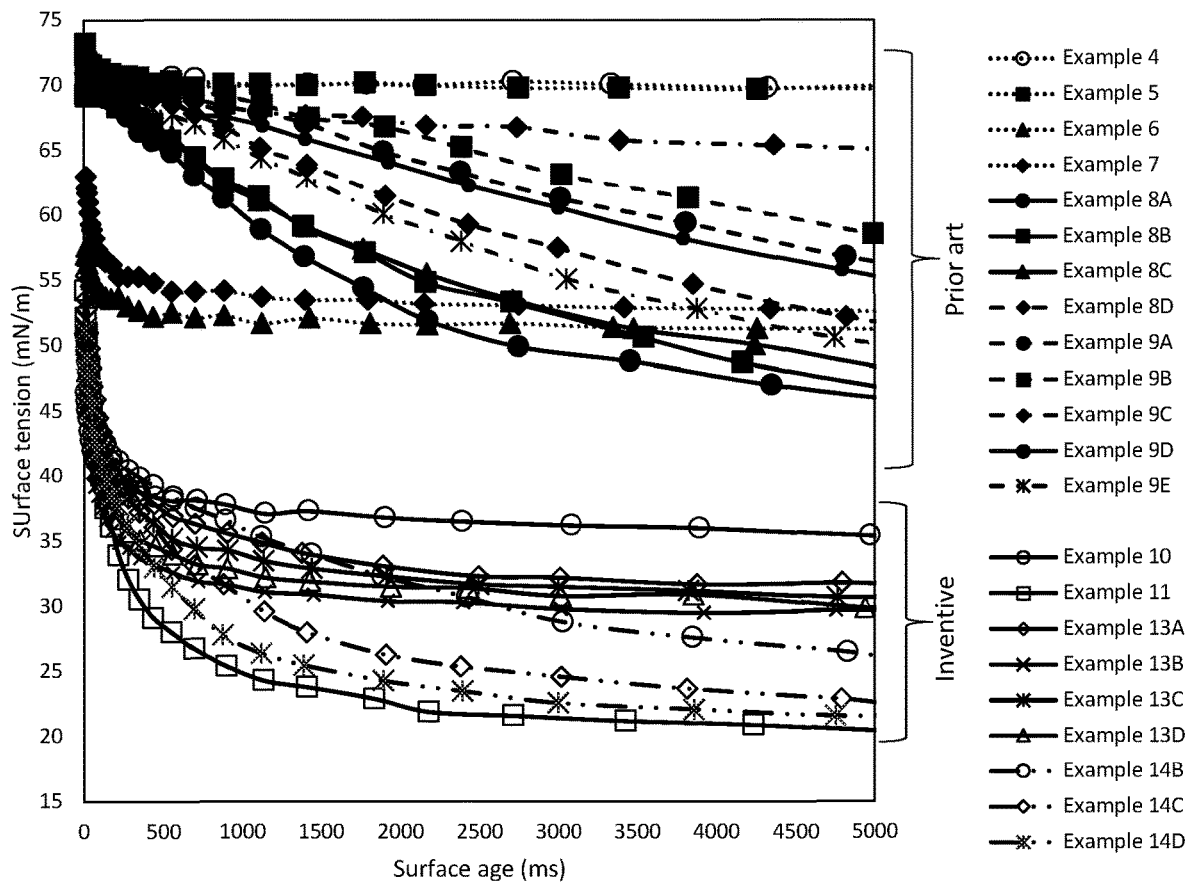
FIG. 3 shows the dynamic surface tension measurements of the inventive disinfectants and comparative prior art disinfectants over a range of surface ages.

FIG. 3 shows a comparison between the dynamic surface tensions over a range of surface ages between several prior art examples of PAA-based disinfectants and the exemplified embodiments of the working disinfectant solution of the invention. As may be clearly seen, the exemplified embodiments all show distinctively faster achievement of surface tensions below about 42.5 mN/m than the prior art examples, reaching surface tensions below 40 mN/m by 5000 ms.

The Wilhelmy plate consists of a thin plate usually on the order of a few square centimetres in area (see FIG. 1). The plate is often made from filter paper, glass or platinum which may be roughened to ensure complete wetting. In fact, the results of the experiment do not depend on the material used, as long as the material is wetted by the liquid. The plate is cleaned thoroughly and attached to a balance with a thin metal wire. The force on the plate due to wetting is measured using a tensiometer or microbalance and used to calculate the surface tension using the Wilhelmy equation:

$$\gamma = \frac{F}{l \cos \theta} \qquad \text{Equation 1}$$

where l is the wetted perimeter and θ is the contact angle between the liquid phase and the plate. In practice the contact angle is rarely measured, instead either literature values are used, or complete wetting is assumed.

One problem with the Wilhelmy plate method is it represents a static case. When a surfactant is dissolved in water, surfactant molecules will migrate to the surface of the liquid (either at the air interface or to the walls of the container). Until a certain concentration of surfactant is reached (the critical micelle concentration, or CMC), all of the molecules of surfactant will migrate to the various surfaces surrounding the solution. Once above the CMC, aggregates of surfactant molecules (micelles) will form within the bulk solution.

The rate of diffusion of surfactant molecules from the bulk solution to the surface interface will vary, dependant on surfactant type, and this will manifest itself in for example, the speed of wetting.

When measured by the Wilhelmy plate method (or similar methods such as the DeNoy ring) the solution being measured is unagitated, and will represent the static, or equilibrium surface tension, i.e. the surface tension achieved once all of the available surfactant molecules have migrated to the interface.

Whilst this measurement will be valid for the assessment of disinfectants used under static conditions (i.e. when for instance the endoscope is immersed into a static solution of disinfectant), this is not the case in modern AER's, which typically pump disinfectant solution continually through the endoscope lumens, and use spray arms to spray the external surfaces of the endoscope with disinfectant. This produces a highly dynamic environment, with constant mixing of the disinfectant. Under these conditions, with a slow diffusing surfactant system, the actual surface tension will be significantly higher than the one measured using a static method such as the Wilhelmy plate.

Dynamic Surface Tension Measurement

One method for measuring the dynamic surface tension is the Maximum Bubble Pressure method. Due to internal attractive forces of a liquid, air bubbles within the liquids are compressed. The resulting pressure (bubble pressure) rises as the bubble radius decreases. The bubble pressure method makes use of this bubble pressure which is higher than in the surrounding environment (water). A gas stream is pumped into a capillary that is immersed in a fluid. The resulting bubble at the end of the capillary tip continually becomes larger in surface area.

Figure 2:
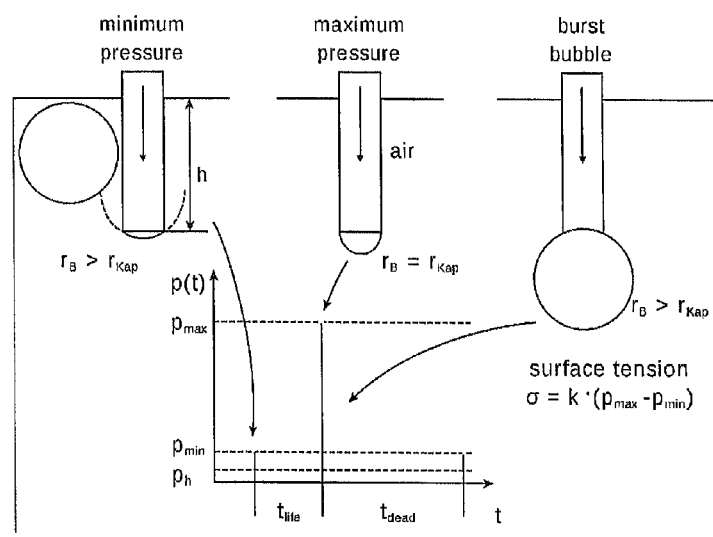
FIG. 2 shows the Maximum Bubble Pressure method for determining the dynamic surface tension of a liquid or solution.

The pressure rises to a maximum level. At this point the bubble has achieved its smallest radius (the capillary radius) and forms a hemisphere. Beyond this point the bubble quickly increases in size and soon bursts, tearing away from the capillary, thereby allowing a new bubble to develop at the capillary tip. It is during this process that a characteristic pressure pattern develops (see FIG. 2), which is evaluated for determining the surface tension.

By varying the speed of bubble formation, the surface tension may be determined over a range of surface ages, with surface tensions measured at longer surface ages approaching the values measured under static conditions.

The use of the maximum bubble pressure method therefore allows the determination of surface tension under dynamic conditions (such as those encountered in a modern AER).

Disinfectant Components
Peracetic Acid Solution

In a preferred embodiment, the disinfectant concentrate of the invention is prepared using an equilibrium solution containing PAA, hydrogen peroxide, acetic acid and water containing between about 0.1 and about 20% w/w PAA. In a more preferred embodiment, the PAA solution will comprise preferably between about 1% and 15% w/w, more preferably about 4% w/w and about 6% w/w PAA.

Typically, a PAA solution will be supplied as an equilibrium solution. These solutions are prepared by reacting hydrogen peroxide with acetic acid, as shown in equation 2.

$$CH_3COOH + H_2O_2 \rightleftharpoons CH_3COOOH + H_2O \qquad \text{Equation 2}$$

The reaction mixture preferably also comprises stabilisers, which are usually chelating agents that serve to complex heavy metal ions in order to prevent them catalysing the degradation of the peroxy species.

The reaction to form PAA may be left uncatalyzed, in which case the reaction can take between 10-15 days to come to equilibrium, or it may be catalysed by the addition of a small (ca 1% w/w) quantity of a strong acid such as sulfuric acid. At equilibrium, the final solution will be comprised of a mixture that contains both the reactants and products (ie a mixture containing PAA, water, hydrogen peroxide and acetic acid). The equilibrium solution may be prepared using known methods (eg the method of F. P. Greenspan, "The Convenient Preparation of Per-acids", J. Am. Chem. Soc. 1946, 68, 5, 907-907)

The extent of the reaction can be defined by an equilibrium constant, k, which is the ratio of the molar concentrations of the products and reactants, i.e.

$$k = \frac{[PAA] \times [Water]}{[HP] \times [AcOH]} \qquad \text{Equation 3}$$

Rearranging this equation gives $$[PAA] = \frac{[HP] \times [AcOH]}{[Water] \times k} \qquad \text{Equation 4}$$

Where:
k is the equilibrium constant
[PAA] is the molar concentration of PAA
[Water] is the molar concentration of water
[HP] is the molar concentration of hydrogen peroxide
[AcOH] is the molar concentration of acetic acid At room temperature, the value of the equilibrium constant will be approximately 2.7 (see for example Zhao et al, "Preparation of Peracetic Acid from Acetic Acid and Hydrogen Peroxide: Experimentation and Modelling", The Chinese Journal of Process Engineering, 8(1), 35-41, (2008)).

As can be seen from Equation 4 the molar concentration of PAA is directly proportional to the product of the molar concentrations of hydrogen peroxide and acetic acid, and inversely proportional to the molar concentration of water in the solution. It follows therefore that an equilibrium solution containing a defined concentration of PAA may contain differing concentrations of hydrogen peroxide and acetic acid, as long as the product of their molar concentrations remain constant.

The PAA composition may also comprise other ingredients such as stabilisers and mineral acids. The stabilizers may be selected from the group consisting of phosphonic acid derivatives, such as amino tri (methylene phosphonic acid), 1-hydroxyl ethylidene-1,1,-diphosphonic acid, quinoline-8-ol, 2,6-pyridinedicarboxylic (dipicolinic) acid, aspartic acid diethoxysuccinate, quinoline-2-carboxylic acid, citric acid, isocitric acid, aconitic acid, propane-1,2,3-tricarboxylic acid and mixtures thereof. The mineral acids may be selected from the group consisting of sulfuric acid, nitric acid, methanesulfonic acid, trifluoromethanesulfonic acid and mixtures thereof.

In yet another embodiment, the PAA comprising the composition of the invention may be formed by the reaction between hydrogen peroxide solution and an acylating agent such as tetraacetyl ethylenediamine (TAED), N-acetyl caprolactam, N-acetyl succinimide, N-acetyl phthalimide, N-acetyl maleimide, penta-acetyl glucose, octaacetyl sucrose, acetylsalicylic acid, tetraacetyl glycouril, and combinations thereof.

When diluted for use, the concentration of PAA within the working disinfectant solution will be preferably between about 0.01% w/v to about 1.0% w/v (about 100 ppm and about 10,000 ppm), and more preferably between about 0.02% w/v to about 0.5% w/v (200 ppm and about 5000 ppm).

As will be recognised by a skilled practitioner, other peracids may be used in conjunction with, or in place of, peracetic acid. These will include, but not limited to, percitric acid, perlactic acid, performic acid, perpropionic acid, perhexanoic acid, perheptanoic acid, peroctanoic acid, perbenzoic acid and mixtures thereof.

Corrosion Inhibitors (Corrosion Inhibiting Agents)

Preferably, the disinfectant composition of the invention comprises a corrosion inhibitor such as, but not limited to, benzotriazole, alkali metal phosphates, alkali metal nitrate salts, alkali metal nitrite salts, 2-phosphonobutane-1,2,4-tricarboxylic acid salts, metal molybdate salts and combinations thereof.

The corrosion inhibitor mitigates corrosion caused by the disinfectant composition of the invention in both endoscopes and endoscope reprocessors. Preferably the corrosion inhibitor is present in an amount of about 0.1% w/v to about 2% w/v in the disinfectant concentrate or about 500 ppm to about 5000 ppm in the diluted, working disinfectant solution.

In one embodiment, the corrosion inhibitor is contained within Part B of the two-part disinfectant concentrate. In another embodiment, the corrosion inhibitor is contained within the peracetic acid solution of the single-part concentrate.

Surfactants

Suitable surfactants used in the working disinfectant solution of the invention include ionic, non-ionic, zwitterionic and amphoteric surfactants, or mixtures thereof. Preferably the surfactant or surfactant mixture will be low foaming and will also serve as a wetting agent.

It is preferred that the surfactant(s) will be present within the working disinfectant solution in an amount of about 0.005% w/v to 0.5% w/v.

Preferably the surfactant(s) will be present within the working disinfectant solution in an amount of about 0.01% w/v to 0.4% w/v.

In the two-part disinfectant concentrate, the surfactant(s) are preferably present in an amount of about 0.05% to about 15% w/w, more preferably about 0.1% to about 10% w/w of the Part B composition.

In the single-part disinfectant concentrate, the surfactant(s) will preferably be present in an amount of about 0.05% to about 15% w/w, more preferably about 0.1% to about 10% w/w of the a single-part disinfectant concentrate.

Ideally the surfactant(s) will also provide for fast wetting of surfaces. In a preferred embodiment, the surfactants will be selected to provide the working disinfectant solution with a Draves wetting time under 40 seconds.

In a preferred embodiment, the surfactants will be selected to provide the working disinfectant solution with a dynamic surface tension less than about 42.5 mN/m at a surface age of 250 ms, and less than about 41 mN/m at a surface age of 500 ms when measured by the Maximum Bubble Pressure method.

More preferably, the surfactants will be selected to provide the working disinfectant solution with a dynamic surface tension less than about 42.5 mN/m at a surface age of 250 ms, less than about 41 mN/m at a surface age of 500 ms at 20-25° C. and less than about 40 mN/m at a surface age of 5000 ms when measured by the Maximum Bubble Pressure method.

Examples of suitable surfactants which may be used in the composition of the invention include but are not limited to block copolymers of polyethylene oxide and polypropylene oxide, fatty alcohol alkoxylates, long chain alkyl alkoxylates, N-alkyl pyrrolidones, branched short chain perfluoro surfactants, branched short chain polysiloxane functionalised polyglycols and combinations thereof.

Hydrotropes

A hydrotrope is a compound that solubilizes hydrophobic compounds in aqueous solutions by means other than micellar solubilization. Typically, hydrotropes consist of a hydrophilic part and a hydrophobic part (similar to surfactants), but the hydrophobic part is generally too small to cause spontaneous self-aggregation.

A hydrotrope may be used within the disinfectant composition of the invention to allow for the solubilisation of otherwise insoluble components such as low foaming non-ionic surfactants.

Suitable hydrotropes may be include but are not limited to, potassium xylene sulfonate, potassium naphthalene sulfonate, potassium cumenesulfonic acid, potassium cresylphosphate, potassium octyliminodipropionate, sodium xylene sulfonate, sodium naphthalene sulfonate, sodium cumenesulfonic acid, sodium cresylphosphate, sodium octyliminodipropionate, pentyl glucoside, hexyl glucoside, octyl glucoside, isooctyl glucoside, and mixtures thereof.

In a preferred embodiment, the hydrotrope is present in an amount of about 0.1% to about 15% w/w, more preferably about 0.5% to about 10% w/w of the Part B of the two-part disinfectant concentrate.

In a second preferred embodiment, the hydrotrope is present in an amount of about 0.1% to about 15% w/w, more preferably about 0.5% to about 10% w/w of equilibrium peracetic acid concentrate of a single-part disinfectant concentrate.

pH Adjusting Agents

The working disinfectant solution of the invention and the disinfectant concentrate may also comprise pH adjusting agents to control the pH of the final disinfectant composition. These pH adjusting agents be selected from the group consisting of alkali metal hydroxides, alkali metal carbonates and alkali metal salts of polyvalent acids, for example alkali metal salts of citric, boric, phosphoric, oxalic, maleic, and fumaric acid.

The pH adjusting agents may be used to control the pH of the Part B of the disinfectant concentrate itself, allowing the use of surfactants that may be acid or base labile. The pH of the Part B disinfectant concentrate is preferably in the range about 6.0 to about 13, more preferably about 7.0 to about 13.

The pH adjusting agent within the Part B may provide a preferred pH to the working disinfectant solution, allowing for the presence of acidic species that may be present in the starting Part A (PAA) solution. The pH of the working disinfectant solution of the invention is preferably in the range about 2.0 to about 8, more preferably about 3.0 to about 6.0.

Two-Part Disinfectant Concentrates

In the two-part disinfectant concentrate, the disinfectant concentrate is supplied as two parts (termed "Part A" and "Part B" for clarity), typically two solutions. Part A typically comprises an aqueous equilibrium solution of PAA, hydrogen peroxide and acetic acid. Part A may also comprise small quantities of other components such as stabilisers or strong acids. The stabilisers may be selected from the group consisting of, but not limited to, amino tri (methylene phosphonic acid), 1-hydroxyl ethylidene-1,1,-diphosphonic acid, quinoline-8-ol, 2,6-pyridinedicarboxylic (dipicolinic) acid, aspartic acid diethoxysuccinate, quinoline-2-carboxylic acid, citric acid, isocitric acid, aconitic acid, propane-1,2,3-tricarboxylic acid and mixtures thereof.

Strong acids may be used as catalysts for the formation of PAA. Strong acids which may be used in the invention may be selected from, but not limited to, sulfuric acid, nitric acid, methanesulfonic acid, trifluoromethanesulfonic acid and mixtures thereof.

Also anticipated is the use of commercially sourced equilibrium solutions of PAA. It is recognised that a commercial grade of PAA will contain stabilising agents and optionally strong acids.

In a preferred embodiment, Part B of the disinfectant concentrate will comprise between about 0.05% w/w and about 15% w/w of surfactant. In a more preferred embodiment, the single-part disinfectant concentrate will comprise between about 0.1% w/w and about 10% w/w of surfactant. In a highly preferred embodiment, the disinfectant concentrate will comprise between about 1% and about 9% w/w surfactant.

Part B of the disinfectant concentrate may comprise other components such as corrosion inhibitors, pH adjusting agents, surfactants, colorants, and indicating agents. Part B may also contain hydroptropes to assist in the solubilisation of the various components of the solution.

In a preferred embodiment, the working disinfectant solution of the invention will be produced by combining portions of the Part A and Part B solutions with water to produce an aqueous based working disinfectant solution. Preferably the ratios of the Part A and Part B solutions will be between about 1:10 to about 10:1 by volume. More preferably, the ratios of the Part A and Part B solutions will be between about 1:5 to about 5:1 by volume. Most preferably the ratios of the Part A and Part B solutions will be about 1:1 by volume.

The resulting diluted or working disinfectant solution preferably will contain between about 0.01% w/v to about 1.0% w/v (100 ppm-10,000 ppm) PAA, more preferably about 0.02% w/v to about 0.5% w/v (200 ppm-5000 ppm) PAA, of the working disinfectant solution.

It will be recognised by a person skilled in the art that the concentration of the active ingredient of a disinfectant (in this case PAA) will be determined by a combination of factors, such as contact time for disinfection, disinfection temperature suitable microbiological testing, and desired microbiological performance (eg high level disinfection or sterilisation).

Other factors may also determine the PAA concentration, such as materials compatibility. For example, the corrosivity of the working disinfectant solution may be reduced by lowering the concentration of PAA whilst increasing the contact time and/or disinfection temperature. Similarly, if the device to be disinfected is relatively impervious to corrosion from the disinfectant, a higher concentration and/ or higher temperature may be used with a shorter disinfection contact time in order to achieve a more rapid disinfection.

Whilst a single-part disinfectant concentrate can offer a degree of convenience to the end user, a two-part disinfectant concentrate offers manufacturing flexibility in that the components of Part B are not required to show long-term stability to oxidation by peracids etc.

Single-Part Disinfectant Concentrate

In the single-part disinfectant concentrate, all of the components are preferably supplied as a single concentrate which is then diluted, preferably with water, prior to use to give the working disinfectant solution. In another embodiment, the single-part disinfectant may be used without dilution (ie a ready to use solution). The resulting working disinfectant solution preferably comprises between about 0.01% w/v to about 1.0% w/v (100 ppm-10,000 ppm) PAA, more preferably about 0.02% w/v to about 0.5% w/v (200 ppm-5000 ppm) PAA, of the working disinfectant solution.

It will be recognised by a person skilled in the art that the concentration of the active ingredient of a disinfectant (in this case PAA) will be determined by a combination of factors, such as contact time for disinfection, disinfection temperature suitable microbiological testing, and desired microbiological performance (eg high level disinfection or sterilisation).

Other factors may also determine the PAA concentration, such as materials compatibility. For example, the corrosivity of the working disinfectant solution may be reduced by lowering the concentration of PAA whilst increasing the contact time and/or disinfection temperature. Similarly, if the device to be disinfected is relatively impervious to corrosion from the disinfectant, a higher concentration and/or higher temperature may be used with a shorter disinfection contact time in order to achieve a more rapid disinfection.

The single-part disinfectant concentrate comprises PAA, hydrogen peroxide, acetic acid. The single-part disinfectant concentrate also comprises at least one surfactant, and optionally corrosion inhibitors, hydrotropes and/or pH buffers, as well as stabilising agents.

In a preferred embodiment, the single part disinfectant concentrate will contain between about 0.1% w/w and 20% w/w peracetic acid.

In a more preferred embodiment, the single part disinfectant concentrate will contain between about 1% w/w and 15% w/w peracetic acid In a highly preferred embodiment, the single part disinfectant concentrate will contain between about 4% w/w and 6% w/w peracetic acid.

The stabilising agents may be selected from the group consisting of, but not limited to, amino tri (methylene phosphonic acid), 1-hydroxyl ethylidene-1,1,-diphosphonic acid, quinoline-8-ol, 2,6-pyridinedicarboxylic (dipicolinic) acid, aspartic acid diethoxysuccinate, quinoline-2-carboxylic acid, citric acid, isocitric acid, aconitic acid, propane-1,2,3-tricarboxylic acid.

Typically, the stabilising agent will be present in concentrations between about 0.1% w/w and about 1% w/w of the single-part disinfectant concentrate.

The single-part disinfectant concentrate may optionally contain strong acids selected from, but not limited to, sulfuric acid, nitric acid, methanesulfonic acid, trifluoromethanesulfonic acid and mixtures thereof. As will be recognised by one skilled in the art, the strong acid may be added to serve as a catalyst during the formation of the PAA solution.

Typically, the acid will be present in concentrations between about 0.1% w/w and about 1% w/w of the single-part disinfectant concentrate.

The single-part disinfectant concentrate may be produced by mixing together hydrogen peroxide, acetic acid, water, stabilising agent, at least one surfactant, and optionally corrosion inhibitors, hydrotropes and/or pH buffers.

The reaction to produce the PAA may be uncatalyzed, whereupon the PAA will form over the course of several days, or catalysed by the addition of a strong acid selected from, but not limited to, sulfuric acid, nitric acid, methanesulfonic acid, trifluoromethanesulfonic acid and mixtures thereof. Typically, the acid will be present in concentrations between about 0.1% w/w and about 1% w/w of the single-part disinfectant concentrate.

In a second embodiment, the single-part disinfectant concentrate may be produced by the addition of at least one surfactant, and optionally corrosion inhibitors, hydrotropes and/or pH buffers to a pre-formed solution of PAA. This pre-formed solution can be commercially sourced. It is recognised that a commercial grade of PAA will contain stabilising agents and optionally strong acids.

In a preferred embodiment, the single-part disinfectant concentrate will comprise between about 0.05% w/w and about 15% w/w of surfactant. In a more preferred embodiment, the single-part disinfectant concentrate will comprise between about 0.1% w/w and about 10% w/w of surfactant. In a highly preferred embodiment, the disinfectant concentrate will comprise between about 1% and about 9% w/w surfactant.

It will be apparent to one skilled in the art that all of the components in the single-part disinfectant concentrate should be stable with respect to oxidation by peroxy species.

Working Disinfectant Solution

A working disinfectant solution is herein defined as the disinfectant formed by the dilution of a disinfectant concentrate, and will be the disinfectant solution used to disinfect reusable thermolabile medical devices such as flexible endoscopes etc.

In the case of a single-part disinfectant concentrate, the working disinfectant solution will be produced by dilution of the single-part disinfectant concentrate.

In the case of a two-part disinfectant concentrate, the working disinfectant solution will be formed by diluting a mixture of the two parts (Parts A and B). Typically, the working disinfectant solution will be formed by adding Parts A and B to the required volume of water to avoid any adverse reaction resulting from mixing the undiluted concentrates together.

In a preferred embodiment, the working disinfectant solution of the invention will be produced by combining portions of the Part A and Part B solutions with water to produce an aqueous based working disinfectant solution. Preferably the ratios of the Part A and Part B solutions will be between about 1:10 to about 10:1 by volume. More preferably, the ratios of the Part A and Part B solutions will be between about 1:5 to about 5:1 by volume. Most preferably the ratios of the Part A and Part B solutions will be about 1:1 by volume.

The concentration of PAA within the working disinfectant solution will be preferably 0.01% w/v to about 1.0% w/v (100 ppm-10,000 ppm) PAA, more preferably about 0.02% w/v to about 0.5% w/v (200 ppm-5000 ppm) PAA, of the working disinfectant solution.

It is recognised that often a more concentrated disinfectant will be used for sterilisation compared to high level disinfection.

The concentration of PAA within the working disinfectant solution when used as a high level disinfection will be preferably 0.01% w/v to about 0.5% w/v (100 ppm-5,000 ppm) PAA, more preferably about 0.02% w/v to about 0.25% w/v (200 ppm-2500 ppm) PAA, of the working disinfectant solution.

The concentration of PAA within the working disinfectant solution when used as a sterilant will be preferably 0.02% w/v to about 1.0% w/v (200 ppm-10,000 ppm) PAA, more preferably about 0.04% w/v to about 0.5% w/v (400 ppm-5000 ppm) PAA, of the working disinfectant solution.

As will be recognised by one skilled in the art, the minimum concentration of PAA will be determined by microbiological testing in accordance with national regulations and will also be determined by temperature of disinfection and/or sterilisation, as well as the contact time for disinfection and/or sterilisation.

For example, the two-part disinfectant Rapicide PA (Medivators Inc, Minneapolis, MN, United States) has a minimum recommended concentration of 850 ppm PAA, with a contact time of 5 minutes at 30° C. for high level disinfection and a minimum recommended concentration of 1700 ppm PAA, with a contact time of 10 minutes at 40° C. for sterilisation. These concentrations will be achieved by the dilution of the Rapicide A and B solutions to 1.7-1.9% v/v for high level disinfection and 3.4-3.8% v/v for sterilisation. In this case, equal volumes of the Part A and B solution will be used.

The working disinfectant solution will also comprise between about 0.05% w/v to about 0.5% w/v of at least one surfactant.

Suitable surfactants used in the working disinfectant solution of the invention include ionic, non-ionic, zwitterionic and amphoteric surfactants, or mixtures thereof. Preferably the surfactant or surfactant mixture will be low foaming and will also serve as a wetting agent.

Examples of suitable surfactants which may be used in the composition of the invention include but are not limited to block copolymers of polyethylene oxide and polypropylene oxide, fatty alcohol alkoxylates, long chain alkyl alkoxylates, N-alkyl pyrrolidones, branched short chain perfluoro surfactants, branched short chain polysiloxane functionalised polyglycols and combinations thereof.

It will also optionally comprise between about 0.01 and about 0.1% of at least one corrosion inhibitor and up to 0.2% of a hydrotrope.

Suitable corrosion inhibitor may be comprised of, but not limited to, benzotriazole, alkali metal phosphates, alkali metal nitrate salts, alkali metal nitrite salts, 2-phosphonobutane-1,2,4-tricarboxylic acid salts, metal molybdate salts and combinations thereof.

Suitable hydrotropes may be include but are not limited to, potassium xylene sulfonate, potassium naphthalene sulfonate, potassium cumenesulfonic acid, potassium cresylphosphate, potassium octyliminodipropionate, sodium xylene sulfonate, sodium naphthalene sulfonate, sodium cumenesulfonic acid, sodium cresylphosphate, sodium octyliminodipropionate, pentyl glucoside, hexyl glucoside, octyl glucoside, isooctyl glucoside, and mixtures thereof.

Other optional components within the working disinfectant solution may include pH adjusting agents, indicators, colourants and perfumes.

Methods Used

Example 1: Determination of Hydrogen Peroxide and PAA

The hydrogen peroxide and PAA content of PAA solutions were determined using a two-stage redox titration using a Mettler Toledo T70 autotitrator. The autotitrator was equipped with two burettes and drive units, a platinum ring redox sensor and peristaltic pump for dispensing auxiliary solutions. One burette was charged with a 0.02M potassium permanganate solution and the second with a 0.1M sodium thiosulfate solution. Both titrants were standardised before use.

A known weight of sample was placed into a titration beaker, along with 20 ml of a 0.5M sulfuric acid solution. The beaker was placed on the autotitrator, and the hydrogen peroxide determined by titration against the potassium permanganate solution. Following identification of the end point, 10 ml of a 10% potassium iodide solution was added via the peristaltic pump (under the control of the T70 autotitrator) and the liberated iodine then titrated using the sodium thiosulfate solution. The concentrations of hydrogen peroxide and PAA were then calculated by the autotitrator, taking into account the excess potassium permanganate added after the endpoint.

Example 2: Determination of Acetic Acid

The acetic acid content of PAA solutions was determined using an acid-base titration using a Mettler Toledo T70 autotitrator fitted with a single burette charged with 0.1M sodium hydroxide solution and a pH sensor.

A known weight of the PAA solution was placed into a titration beaker, and approximately 30 ml DI water added. The beaker was then placed on the autotitrator and the sample titrated against the 0.1M sodium hydroxide solution.

Example 3: Measurement of Dynamic Surface Tension

The dynamic surface tension of the various disinfectant solutions was determined over a range of surface ages (typically 14 ms to 5000 ms) using a Krüss BP50 Bubble tensiometer (Krüss GMBH, Hamburg, Germany). A fresh capillary tip was fitted to the BP50 for each set of measurements performed, with the instrument being recalibrated using HPLC water each time the capillary tip was changed.

Data from the BP50 was acquired by Laboratory Desktop version 3.2.2.3064, a software package supplied by Krüss.

The surface tensions at specific surface ages were calculated by interpolation of the data points either side of the specific age. For example, the surface tension at 500 ms may be calculated from the surface tension values of 29.1 and 28.0 mN/m at surface ages of 440 ms and 555 ms respectively by assuming linearity between these two points and determining the slope and intercept of the straight line between these two points. In the example above, the surface tension at 500 ms may be calculated as 28.5 mN/m.

Prior Art Examples

FIG. 3 shows a comparison between the dynamic surface tensions over a range of surface ages between several prior art examples of PAA-based disinfectants and the exemplified embodiments of the working disinfectant solution of the invention. As may be clearly seen, the exemplified embodiments all show distinctively faster achievement of surface tensions below about 42.5 mN/m than the prior art examples, reaching surface tensions below 40 mN/m by 5000 ms.

Examples 4 to 6 represent commercial PAA based High Level Disinfectants intended for use in Automated Endoscope Reprocessors Example 4

1.9 ml of Proxy P (a 5% w/w PAA solution supplied by Whiteley Corporation, Tomago, NSW, Australia)) was pipetted into a 100 ml volumetric flask containing ca 80 ml tap water. 1.9 ml of Proxy A (a corrosion inhibitor concentrate) was then added by pipette, and the solution made up to the mark with additional tap water to form a working disinfectant solution.

Figure 4:
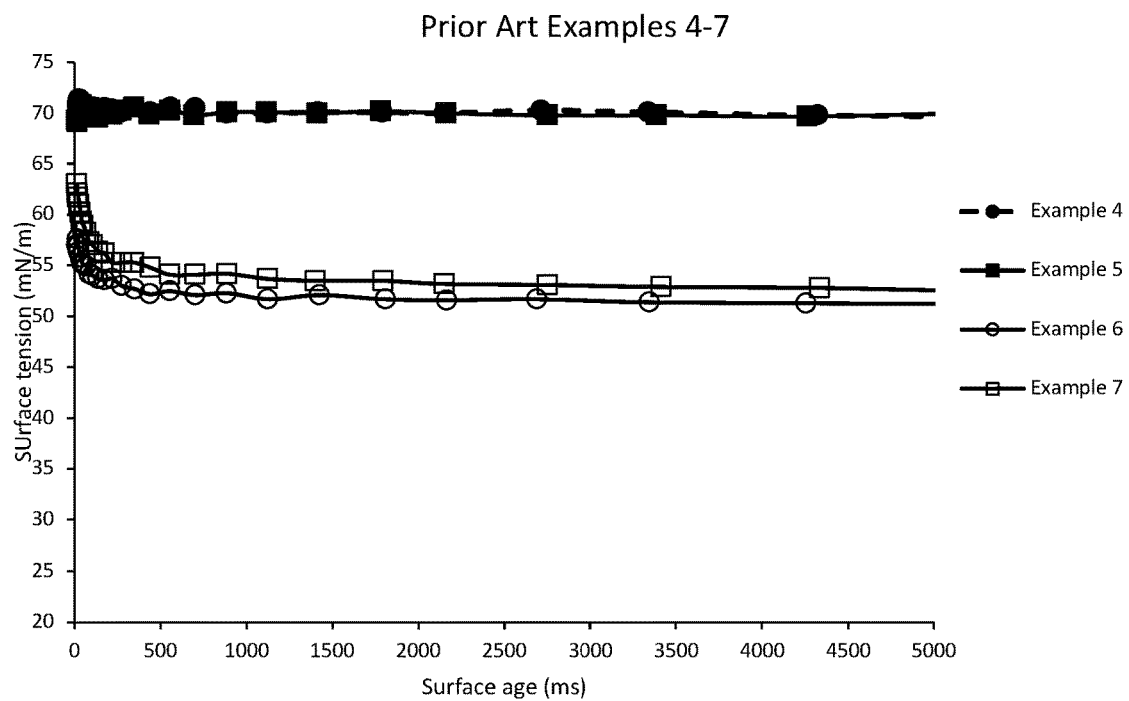
FIG. 4 shows the dynamic surface tension measurements of various prior art disinfectants exemplified as Examples 4-7 over a range of surface ages.

The surface tension of the resultant working disinfectant solution was then measured over a range of surface ages (14 ms-5000 ms) following the procedure outlined in Example 3. As can be seen in FIG. 4 and Table 2, there is substantially no lowering of the surface tension of the disinfectant (the surface tension of pure water is 72 mN/m, and no significant variance in surface tension with surface age.

TABLE 2

| Surface age (ms) | Dynamic Surface tension (mN/m) |
|---|---|
| 250 | 70.2 |
| 500 | 70.4 |
| 5000 | 69.7 |

Example 5

1.9 ml of Soluscope P (a 5% w/w PAA solution supplied by Soluscope SAS, France), was pipetted into a 100 ml volumetric flask containing ca 80 ml tap water. 1.9 ml of Soluscope A (a corrosion inhibitor concentrate) was then added by pipette, and the solution made up to the mark with additional tap water.

The surface tension of the resultant working disinfectant solution was then measured over a range of surface ages (14 ms-5000 ms) as described in Example 3. As can be seen in FIG. 4 and Table 3, there is again substantially no lowering of the surface tension of the disinfectant from that of water (ie 72 mN/m).

TABLE 3

| Surface age (ms) | Dynamic Surface Tension (mN/m) |
|---|---|
| 250 | 70.1 |
| 500 | 70.1 |
| 5000 | 69.9 |

Example 6

1.9 ml of Rapicide PA Part A (a 5% w/w PAA solution supplied by Medivators Inc, Minneapolis, MN, United States) was pipetted into a 100 ml volumetric flask containing ca 80 ml tap water. 1.9 ml of Rapicide PA Part B (a corrosion inhibitor concentrate) was then added by pipette, and the solution made up to the mark with additional tap water.

The dynamic surface tension of the resultant working disinfectant solution was measured over the range 14 ms-5000 ms. As may be seen in FIG. 4 and in Table 4, there was an initial rapid drop in surface tension to around 52 mN/m, with the surface tension remaining above 50 mN/m, even at long surface ages (ie >5000 ms).

TABLE 4

| Surface age (ms) | Dynamic Surface tension (mN/m) |
|---|---|
| 250 | 53.3 |
| 500 | 52.5 |
| 5000 | 51.0 |

Example 7

In this example the single-part disinfectant concentrate described in WO2016100818 was prepared. 560.02 g of a 50% solution of hydrogen peroxide was added to 250 ml of HPLC grade water (Sigma Aldrich), followed by 160.00 g of glacial acetic acid, 10.00 g of Dequest 2010 (IMCD, Mulgrave, VIC Australia) and 20 g of Pluronic 10R5 (Sigma Aldrich, Castle Hill, NSW, Australia). The mixture was then stood for at least 2 weeks to allow the formation of PAA.

After 2 weeks the hydrogen peroxide and PAA content was determined using the method of Example 1, and the acetic acid determined using the method of Example 2. The composition of the resultant disinfectant concentrate is shown in Table 5.

TABLE 5

| Ingredient | Concentration (% w/w) |
|---|---|
| Hydrogen peroxide | 24.20 |
| PAA | 7.10 |
| Acetic acid | 10.93 |
| Pluronic 10R5 | 2.00 |
| Dequest 2010 | 1.00 |
| Water | balance |

2 ml of this formulation was then pipetted into a 100 ml volumetric flask and made up to the mark with tap water. The dynamic surface tension of the resultant working disinfectant solution was then measured following the method of example 3.

TABLE 6

| Surface age (ms) | Dynamic Surface Tension (mN/m) |
|---|---|
| 250 | 55.3 |
| 500 | 54.4 |
| 5000 | 52.6 |

As may be seen in FIG. 4 and in Table 6, despite a relatively rapid initial fall in surface tension to a value of 54.4 at a surface age of 500 ms, the surface tension effectively holds steady with only a slight difference in surface tensions between 500 and 5000 ms.

Example 8

The following examples represent prior art examples drawn from U.S. Pat. No. 6,168,808. Four formulations were prepared according to Table 7.

TABLE 7

| | Proxitane (g) | Genapol EP2564 (g) | Ammonyx LO (g) |
|---|---|---|---|
| Example 8A | 99.4 | 0.25 | 0.30 |
| Example 8B | 99.56 | 0.25 | 0.20 |
| Example 8C | 99.66 | 0.25 | 0.10 |
| Example 8D | 99.75 | — | 0.25 |

The PAA solution used is an equilibrium solution supplied by Solvay Interox Pty Ltd (Banksmeadow, NSW, Australia). This PAA solution contains 5% PAA, 27% hydrogen peroxide and 7.5% acetic acid.

In these examples, Genapol EP2564 (Clariant Pty Ltd, Lara, VIC Australia) was used. This surfactant was formerly known under the trade name Genapol 2908D. Ammonyx LO is a cocodimethylamine oxide supplied by Ixom Operations Pty Ltd, East Melbourne, VIC, Australia.

2 ml of each solution was pipetted into a 100 ml volumetric flask and diluted to the mark with tap water.

Figure 5:
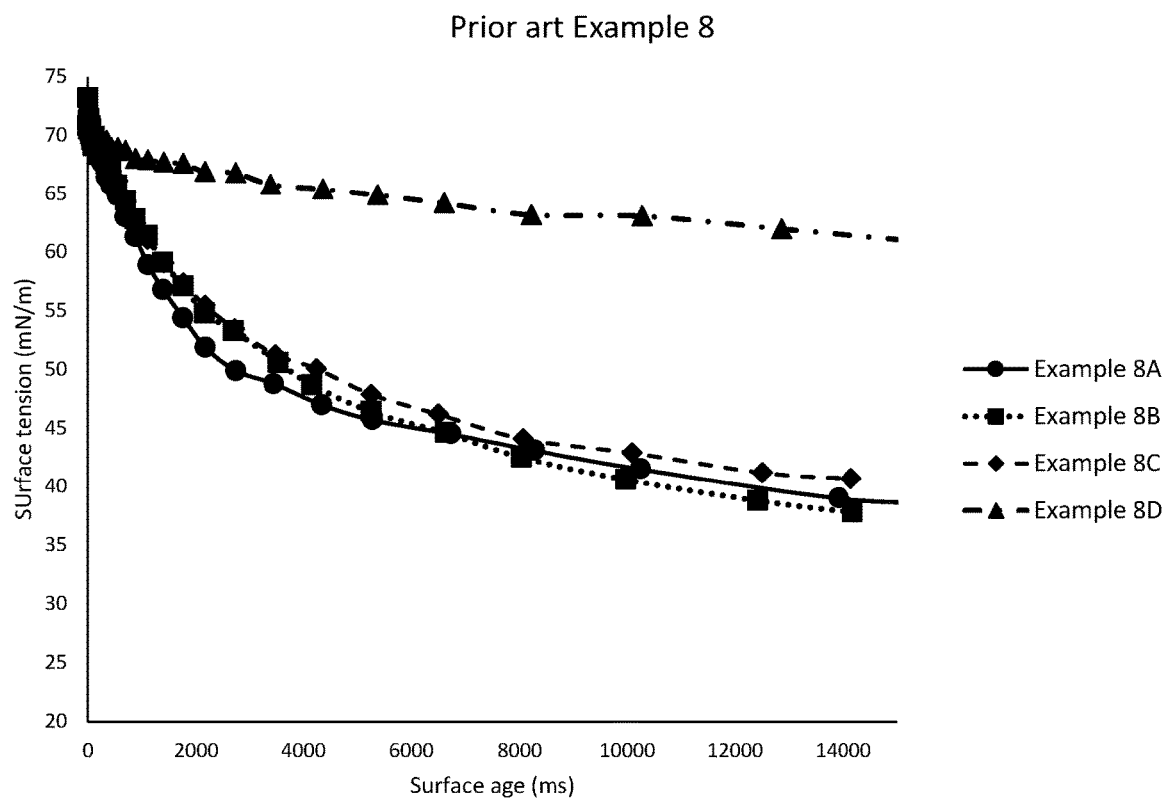
FIG. 5 shows the dynamic surface tension measurements of various prior art disinfectants according to U.S. Pat. No. 6,168,808 exemplified as Examples 8A-8D over a range of surface ages.

The dynamic surface tension of each diluted solution was assessed following the method of Example 3. The dynamic surface tension plots for these examples are shown in FIG. 5, and the surface tensions at 250, 500 and 5000 ms are given in Table 8. As may be seen, the fall in surface tension over the first 500 ms with each formulation is slow. By 5000 ms, the surface tensions of each formulation is still above 45 mN/m.

TABLE 8

| Surface Age (ms) | Dynamic Surface tension (mN/m) | | | |
| --- | --- | --- | --- | --- |
| | 8A | 8B | 8C | 8D |
| 250 | 67.9 | 68.2 | 68.8 | 69.5 |
| 500 | 65.2 | 66.3 | 66.5 | 69.0 |
| 5000 | 46.1 | 47.0 | 48.5 | 65.1 |

Example 9

The following examples were taken from EP0971584. As each example given in the '584 document was prepared from a PAA solution of differing compositions, the various PAA solutions were prepared as shown below.

Preparation of PAA Samples

A series of PAA solutions were prepared by mixing deionised water, 50% hydrogen peroxide solution and glacial acetic acid. 1-hydroxyethylidene-1,1-diphosohonic acid (HEDP) was added to each formulation as a stabiliser (see Table 9 for quantities).

TABLE 9

| Sample | Water | 50% Hydrogen peroxide | Acetic Acid | HEDP |
| --- | --- | --- | --- | --- |
| Tg-35-31A | 211.0 | 203.17 | 104.25 | 5.07 |
| Tg-35-31B | 287.08 | 178.04 | 44.90 | 5.02 |
| Tg-35-31C | 262.07 | 211.87 | 34.88 | 4.99 |
| Tg-35-31D | 262.03 | 211.07 | 51.33 | 5.02 |
| Tg-35-31E | 270.86 | 165.35 | 73.45 | 5.00 |

The solutions were left to stand at room temperature for 2-3 weeks to allow the systems to reach equilibrium. Each sample was then analysed for PAA and hydrogen peroxide using the method given in Example 1. The acetic acid content of the samples was determined using the method described in example 2.

The compositions of each PAA sample are shown in Table 10.

TABLE 10

| Sample | HP (% w/w) | PAA (% w/w) | Acetic acid (% w/w) |
| --- | --- | --- | --- |
| Tg-35-31A | 15.9 | 5.9 | 15.3 |
| Tg-35-31B | 15.9 | 2.4 | 7.5 |
| Tg-35-31C | 19.2 | 2.0 | 5.6 |
| Tg-35-31D | 18.4 | 3.0 | 7.9 |
| Tg-35-31E | 14.2 | 2.8 | 10.8 |

The PAA solutions were then used to reproduce compositions 1-5 shown in Table A of EP0971584 (see Table 11).

TABLE 11

| Sample | EP0971584 Composition No | PAA Sample | PAA quantity (% w/w) | Genapol Surfactant | Quantity added (% w/w) |
| --- | --- | --- | --- | --- | --- |
| 9A | Composition 1 | Tg-35-31A | 99.75 | EP2564 | 0.25 |
| 9B | Composition 2 | Tg-35-31B | 99.88 | EP2564 | 0.12 |
| 9C | Composition 3 | Tg-35-31C | 99.84 | EP2584 | 0.16 |
| 9D | Composition 4 | Tg-35-31E | 99.87 | EP2564 | 0.13 |
| 9E | Composition 5 | Tg-35-31D | 99.84 | EP2584 | 0.16 |

Notes:
Genapol EP2564, now supplied by Clariant (Australia) Pty Ltd, Lara, VIC, Australia was formerly known as Genapol 2908D.
Genapol EP2584, now supplied by Clariant (Australia) Pty Ltd, Lara, VIC, Australia was formerly known as Genapol 2909.

1.25 ml of sample 9A was diluted to 100 ml with tap water to give a 1 part in 80 dilution working disinfectant solution as per EP0971584. Similarly, 2.5 ml of samples 9B-9E were diluted to 100 ml with tap water to give a 1 part in 40 dilution working disinfectant solution as per EP0971584.

The dynamic surface tensions of the resultant diluted solutions were then measured as described in Example 3.

Figure 6:
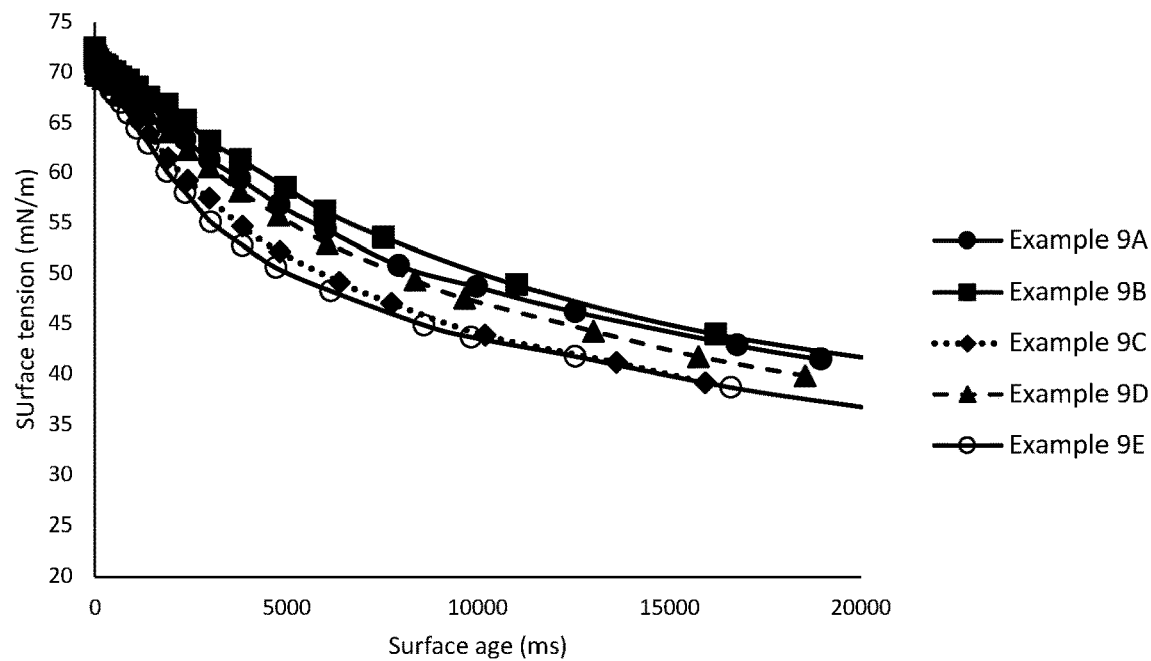
FIG. 6 shows the dynamic surface tension measurements of various prior art disinfectants according to European Patent EP0971584 exemplified as Examples 9A-9E over a range of surface ages.

As may be seen in FIG. 6 and Table 12, whilst the surface tensions of the various working disinfectant solutions 9A to 9E do reach low (<45 mN/m) values, this is only achieved at prolonged surface ages (>15000 ms).

TABLE 12

| Surface age (ms) | Dynamic surface tension (mN/m) | | | | |
| --- | --- | --- | --- | --- | --- |
| | 9A | 9B | 9C | 9D | 9E |
| 250 | 70.3 | 70.6 | 70.1 | 69.6 | 69.4 |
| 500 | 69.6 | 70.1 | 68.9 | 68.9 | 67.9 |
| 5000 | 56.4 | 58.5 | 51.9 | 55.3 | 50.2 |
| 5000 | 44.3 | 45.2 | 40.0 | 42.5 | 39.9 |

It is interesting to note that the observed surface tensions measured using the Maximum Bubble Pressure method are significantly higher than those reported in EP0971584 for the same formulations when measured by a static method (the Wilhelmey plate method), as shown in Table 1.

Inventive Examples

The following examples represent non-limiting embodiments of the present invention. These examples are representative of two-part disinfectants and are intended to be mixed with a PAA solution to form the actual disinfectant.

Example 10

100 ml of the composition shown in Table 13 was prepared

The Triton H66, (a solution of potassium cresylphosphate) was obtained from Dow Chemicals. The Pluronic PE6400, a triblock copolymer of polyethylene oxide and polypropylene oxide was obtained from BASF. Makon NF12 is a low foaming C10-C12 alcohol alkoxylate sourced from Stepan Company, (Northfield, IL, USA), and Surfadone LP100 is a low foaming, nonionic rapid wetting agent comprising N-octyl-2-pyrrolidone having no critical micelle concentration, sourced from Ashland Global Holdings, (Covington, KY, USA). The formulation has a pH of 11.93

TABLE 13

| Ingredient | Weight (g) | Function |
| --- | --- | --- |
| Deionised water | 87.60 | Solvent |
| Dipotassium hydrogen phosphate | 4.46 | pH Buffering agent |
| 48% potassium hydroxide solution | 2.99 | pH adjusting agent |
| Benzotriazole | 1.00 | Corrosion inhibitor |
| Sodium molybdate | 0.26 | Corrosion inhibitor |
| Triton H66 | 2.50 | Hydrotrope |
| Pluronic PE6400 | 4.75 | Surfactant |
| Makon NF12 | 0.25 | Defoaming surfactant |
| Surfadone LP100 | 2.00 | Surfactant/wetting agent |

2 ml of the formulation of Example 10 was pipetted into a 100 ml volumetric flask containing ca 80 ml of tap water. To this was added 2 ml of Rapicide PA Part A, a 5% w/w PAA solution obtained from Cantel Australia, (Heatherton, VIC, Australia). The resultant solution was then made up to the mark with additional tap water to produce the working disinfectant solution. The pH of the diluted solution was 4.04.

The working disinfectant solution contained 0.025% corrosion inhibitors (benzotriazole and sodium molybdate, 0.14% surfactant (Pluronic PE6400, Makon NF12 and Surfadone LP100), 0.05% hydrotrope (Triton H66), along with 2% Proxitane (ie 0.1% PAA)

Figure 7:
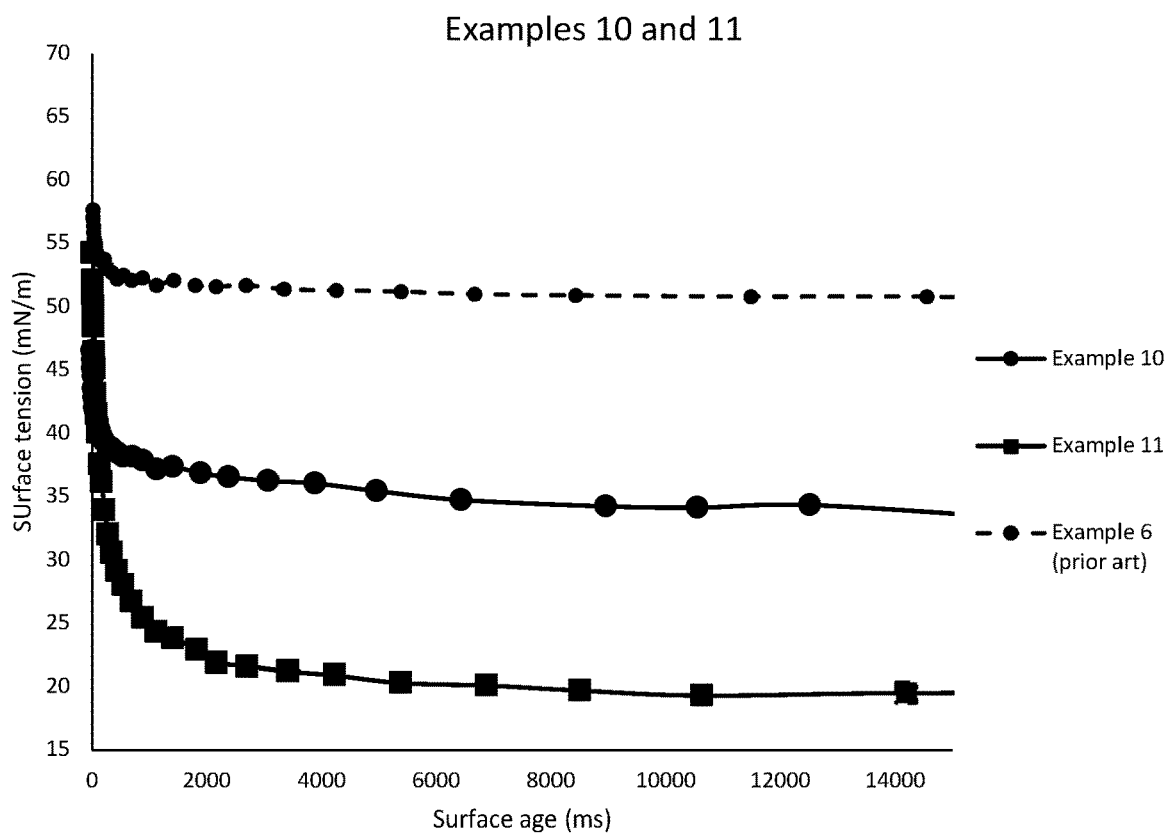
FIG. 7 shows the dynamic surface tension measurements of two embodiments of the present invention (Examples 10 and 11) over a range of surface ages.

The dynamic surface tension of the working disinfectant solution was then measured as described in Example 3. FIG. 7 shows a plot of surface tension in mN/m vs surface age (in milliseconds), and Table 14 shows the surface tension at selected surface ages.

TABLE 14

| Surface age (ms) | Dynamic Surface tension (mN/m) |
| --- | --- |
| 250 | 39.5 |
| 500 | 38.5 |
| 5000 | 35.9 |

Example 11

The following example demonstrates the use of a branched short chain nonionic surfactant, commonly referred to as "superspreaders". Because of the acid-labile nature of the silicone based hydrophobic moiety, the concentrate was formulated to give a pH neutral solution.

100 ml of the following formulation was prepared

TABLE 15

| Ingredient | Weight (g) | Function |
| --- | --- | --- |
| DI water | 869.20 | Solvent |
| Disodium hydrogen phosphate dihydrate | 25.00 | pH Buffering agent |
| Benzotriazole | 5.00 | Corrosion inhibitor |
| Sodium dihydrogen phosphate | 4.00 | pH Buffering agent |
| FC-41 | 30.00 | Hydrotrope |
| Triton H66 | 20.00 | Hydrotrope |
| Orthowet H-408 | 40.00 | Silicone surfactant |
| Emulan TXO | 20.00 | Defoaming surfactant |
| Acticide B20 | 1.00 | Preservative |

FC-41 is a low foaming iso-octyl glucoside, obtained from Interchem Pty Ltd, Abbotsford, VIC, Australia. Orthowet H-408, obtained from Ortho Chemicals, Kensington Victoria, Australia is a solution of 3-(Polyoxyethylene) propylheptamethyltrisiloxane. This surfactant is an example of a class of silicone-based surfactants known as Superspreaders due to their ability to confer rapid wetting and low surface tensions to aqueous solutions. Acticide B20 is a glycol based benzisothiazolinone preservative solution from Thor Specialties Pty Limited, Wetherill Park, NSW, Australia.

The pH of the neat solution was set at 7.32, in order to prevent hydrolysis on storage of the Orthowet H-408.

2 ml of the formulation shown in Table 15 was pipetted into a 100 ml volumetric flask containing ca 80 ml of tap water. To this was added 2 ml of Proxitane, a 5% w/w PAA solution. The resultant solution was then made up to the mark with additional tap water to produce the working disinfectant solution. The pH of the diluted solution was 2.98

Similarly prepared, were working disinfectant solutions using 0.5%, 1.0% and 1.5% of the formulation of Table 15, containing 0.5%, 1.0% and 1.5% Proxitane respectively. The concentrations of each functional ingredient (corrosion inhibitor, surfactant, hydrotrope and PAA) is shown in Table 16.

TABLE 16

| | | Dilution | | | |
| --- | --- | --- | --- | --- | --- |
| | concentrate | 0.5% w/v | 1% w/v | 1.5% w/v | 2% w/v |
| Corrosion inhibitor | 0.49 | 0.00 | 0.00 | 0.01 | 0.01 |
| Surfactant | 5.92 | 0.03 | 0.06 | 0.09 | 0.12 |
| Hydrotrope | 4.93 | 0.02 | 0.05 | 0.07 | 0.10 |
| PAA | n/a | 0.030 | 0.060 | 0.090 | 0.120 |

The dynamic surface tensions of the working disinfectant solutions were then measured as described in example 3. FIG. 7 shows a plot of surface tension in mN/m vs surface age (in milliseconds) for the 2% solution, and Table 17 shows the surface tension at selected surface ages for each concentration.

TABLE 17

| | Dynamic surface tension (mN/m) | | | |
| --- | --- | --- | --- | --- |
| Surface age (ms) | 0.5% | 1.0% | 1.5% | 2.0% |
| 250 | 48.3 | 39.3 | 34.9 | 32.6 |
| 500 | 41.3 | 33.9 | 30.2 | 28.6 |
| 5000 | 25.5 | 21.9 | 20.8 | 20.3 |

The dynamic surface tension of the working disinfectant solutions were then measured using a Krüss BP50 bubble tensiometer as described in example 3. FIG. 7 shows a plot of surface tension in mN/m vs surface age (in milliseconds) for the 2% solution, and Table 16 shows the surface tension at selected surface ages for each concentration.

Example 12

In this example, the effects of the various components of Example 10 were examined.

A base solution comprising 907.77 g deionised water, 46.22 g of anhydrous dipotassium hydrogen phosphate, 30.98 g of 48% w/w potassium hydroxide solution and 10.36 g benzotriazole was prepared.

Various formulations according to Table 18 were then prepared using the base solution. Where possible, the formulations containing only one additional component selected from Triton H66, Pluronic PE6400, Surfadone LP100 and Makon NF12 were also prepared.

In the case of Surfadone LP100 and Makon NF12, these surfactants were insoluble in the base formulation, and so were solublised using the hydrotrope, Triton H66 (see formulations 12-D and 12-F).

TABLE 18

| | Concentration (w/v) | | | | | | |
|---|---|---|---|---|---|---|---|
| Ingredient | 12-A | 12-B | 12-C | 12-D | 12-E | 12-F | 12-G |
| Base solution | 96.05 | 96.05 | 96.05 | 96.05 | 96.05 | 96.05 | 96.05 |
| Triton H66 | — | 2.5 | — | 2.5 | 2.5 | 2.5 | 2.5 |
| Pluronic PE6400 | — | — | 4.75 | — | — | — | 4.75 |
| Makon NF12 | — | — | — | 0.25 | — | 0.25 | 0.25 |
| Surfadone LP100 | — | — | — | — | 2 | 2 | 2 |
| Deionised water | 9.5 | 7 | 4.75 | 6.75 | 5 | 4.75 | — |

From each of these solutions was prepared dilute solutions containing 2% v/v of the various formulations, along with 2% v/v of Rapicide PA Part A, as described in Example 10. The surface tensions at various surface ages for each working disinfectant solution were measured as per Example 3.

Figure 8:
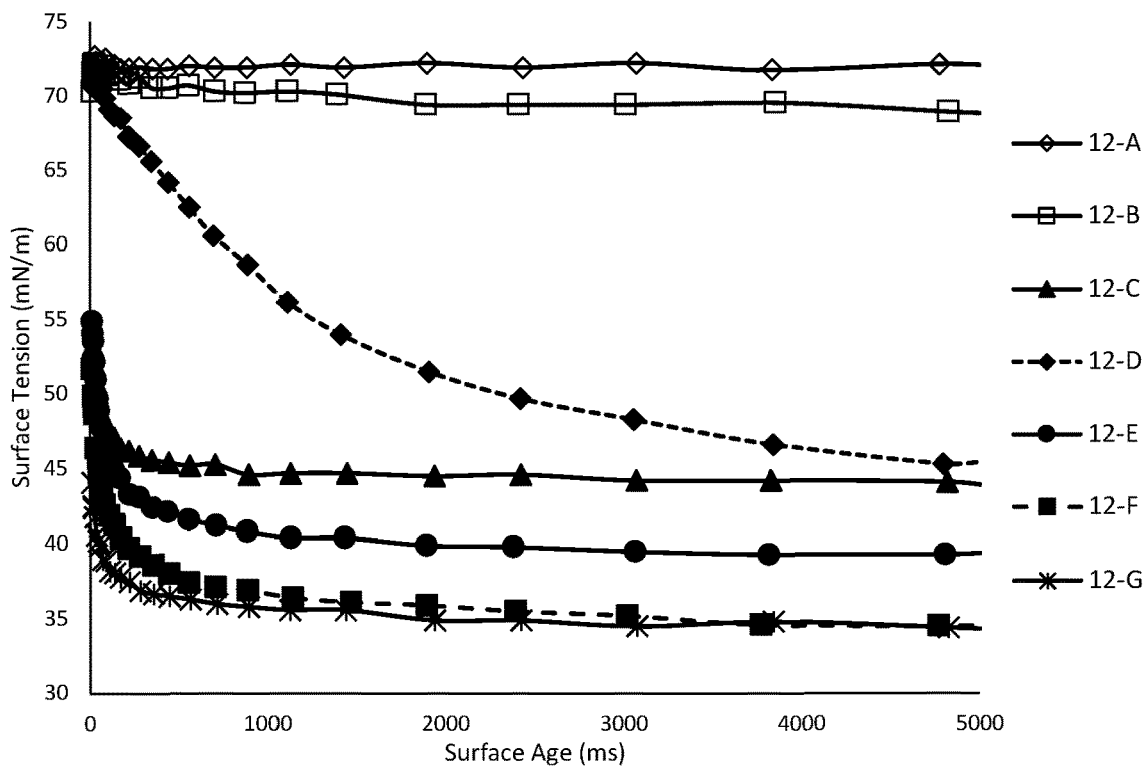
FIG. 8 shows the dynamic surface tension measurements of the various components of Example 10 over a range of surface ages, as described in Example 12.

As may be seen in FIG. 8 and in Table 19, the addition of Triton H66 to the base solution has very little effect on the dynamic surface tension.

The addition of Pluronic PE6400 (see formulation 12-C) does provide a rapid drop in surface tension to 45.4 mN/m at a surface age of 500 ms, but then substantially holds this value, giving a surface tension of 43.9 mN/m at 5000 ms.

The addition of Surfadone LP100 appears to work synergistically with these various formulations, leading to a rapid drop in surface tension to values substantially lower than those seen with e.g. Pluronic PE6400 alone. For example, the addition of Surfadone LP100 to the formulation of 12-C lowers the surface tension at a surface age of 250 ms from 46 mN/m to 38 mN/m.

TABLE 19

| | Dynamic Surface tension (mN/m) | | | | | | |
|---|---|---|---|---|---|---|---|
| Surface age (ms) | 12-A | 12-B | 12-C | 12-D | 12-E | 12-F | 12-G |
| 250 | 71.9 | 71 | 46 | 66.9 | 43.2 | 39.4 | 37.2 |
| 500 | 71.9 | 70.6 | 45.4 | 63.4 | 41.8 | 37.7 | 36.4 |
| 5000 | 72 | 68.8 | 43.9 | 45.5 | 39.4 | 34.6 | 34.3 |

Example 13

In these examples, a fast wetting surfactant, Ecosurf LFE-635, a branched alcohol alkoxylate (Dow Chemicals Co. Ltd) is used to provide the rapid wetting, with Triton H66 used as a hydrotrope.

Varying concentrations, ranging from 2.5% w/v to 5% w/v Ecosurf LFE-635 were prepared as shown in Table 20

TABLE 20

| | 13-A | 13-B | 13-C | 13-D |
|---|---|---|---|---|
| DI water | 92.75 | 92.31 | 91.43 | 90.55 |
| Trisodium phosphate | 4.00 | 4.00 | 4.00 | 4.00 |
| Benzotriazole | 0.60 | 0.60 | 0.60 | 0.60 |
| Sodium molybdate | 0.50 | 0.50 | 0.50 | 0.50 |

TABLE 20-continued

| | 13-A | 13-B | 13-C | 13-D |
|---|---|---|---|---|
| Triton H66 | 5.00 | 5.00 | 5.00 | 5.00 |
| Ecosurf LFE-635 | 2.50 | 3.00 | 4.00 | 5.00 |

TABLE 20-continued

| | 13-A | 13-B | 13-C | 13-D |
|---|---|---|---|---|
| pH concentrate | 11.70 | 11.71 | 11.70 | 11.70 |
| pH (2% v/v + 2% v/v Proxitane) | 4.40 | 4.40 | 4.39 | 4.40 |

2 ml of the formulations were then pipetted into a 100 ml volumetric flask containing ca 80 ml of tap water. 2 ml of Proxitane was then added, and the solution made up to the mark with additional tap water to form the working disinfectant solutions. Table 21 shows the functional components of the working disinfectant solutions.

TABLE 21

| | 13-A | 13-B | 13-C | 13-D |
|---|---|---|---|---|
| Corrosion inhibitor content (% w/v) | 0.022 | 0.022 | 0.022 | 0.022 |
| Surfactant (% w/v) | 0.05 | 0.06 | 0.08 | 0.1 |
| Hydrotrope (% w/v) | 0.1 | 0.1 | 0.1 | 0.1 |
| PAA (% w/v) | 0.1 | 0.1 | 0.1 | 0.1 |

The dynamic surface tensions of the working disinfectant solutions were then measured as described in Example 3.

Figure 9:
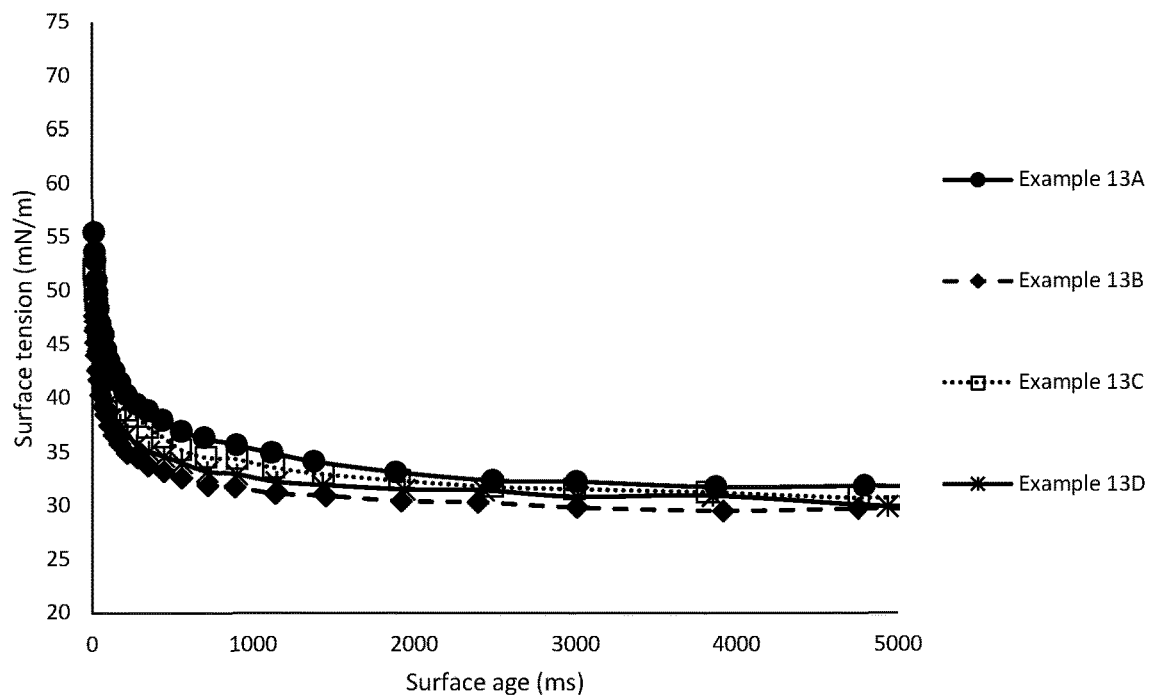
FIG. 9 shows the dynamic surface tension measurements of embodiments of the present invention based on a branched alkyl alkoxylate (Examples 13A-13D) over a range of surface ages.

FIG. 9 shows a plot of surface tension in mN/m vs surface age (in milliseconds), and Table 22 shows the surface tension at selected surface ages. As can be seen, these formulations provide for a rapid drop in surface tension with very short surface ages.

TABLE 22

| | Dynamic Surface tension (mN/m) | | | |
|---|---|---|---|---|
| Surface age (ms) | 13-A | 13-B | 13-C | 13-D |
| 250 | 39.8 | 34.7 | 38.6 | 36.2 |
| 500 | 37.4 | 32.9 | 35.8 | 34.3 |
| 5000 | 31.7 | 29.7 | 30.8 | 29.9 |

Single-Part Disinfectants

The following embodiments of the invention demonstrate single-part formulations, that is formulations comprising a single solution based on a solution of 5% PAA. The PAA solution used was Proxitane.

Example 14

The following examples of a single-part disinfectant are based on the use of Bayhibit AM as a corrosion inhibitor, and Pluronic PE6400 as a solubilising surfactant. A branched short-chain anionic perfluorosurfactant (Tivida FL2200, Merck Pty Ltd, Bayswater, VIC, Australia) was used as the fast-wetting agent. A series of formulations as shown in Table 23 were prepared. Each formulation was observed to be water white, with no apparent haziness

TABLE 23

|  | Composition (% w/w) | | | |
| --- | --- | --- | --- | --- |
|  | 14-A | 14-B | 14-C | 14-D |
| Proxitane | 93.50 | 93.00 | 92.50 | 92.00 |
| Bayhibit AM | 1.00 | 1.00 | 1.00 | 1.00 |
| Pluronic PE6400 | 5.00 | 5.00 | 5.00 | 5.00 |
| Tivida FL2200 | 0.50 | 1.00 | 1.50 | 2.00 |

2 ml of each formulation were pipetted into 100 ml volumetric flasks containing ca 80 ml tap water. The solutions were then made up to the mark with additional tap water to form the working disinfectant solutions. The approximate functional compositions of the working solutions are shown in Table 24

TABLE 24

|  | 14-A | 14-B | 14-C | 14-D |
| --- | --- | --- | --- | --- |
| Corrosion inhibitor content (% w/v) | 0.02 | 0.02 | 0.02 | 0.02 |
| Surfactant (% w/v) | 0.11 | 0.12 | 0.13 | 0.14 |
| Hydrotrope (% w/v) | 0.01 | 0.02 | 0.03 | 0.04 |
| PAA (% w/v) | 0.09 | 0.09 | 0.09 | 0.09 |

The dynamic surface tension of the working disinfectant solutions were then measured as described in Example 3.

Figure 10:
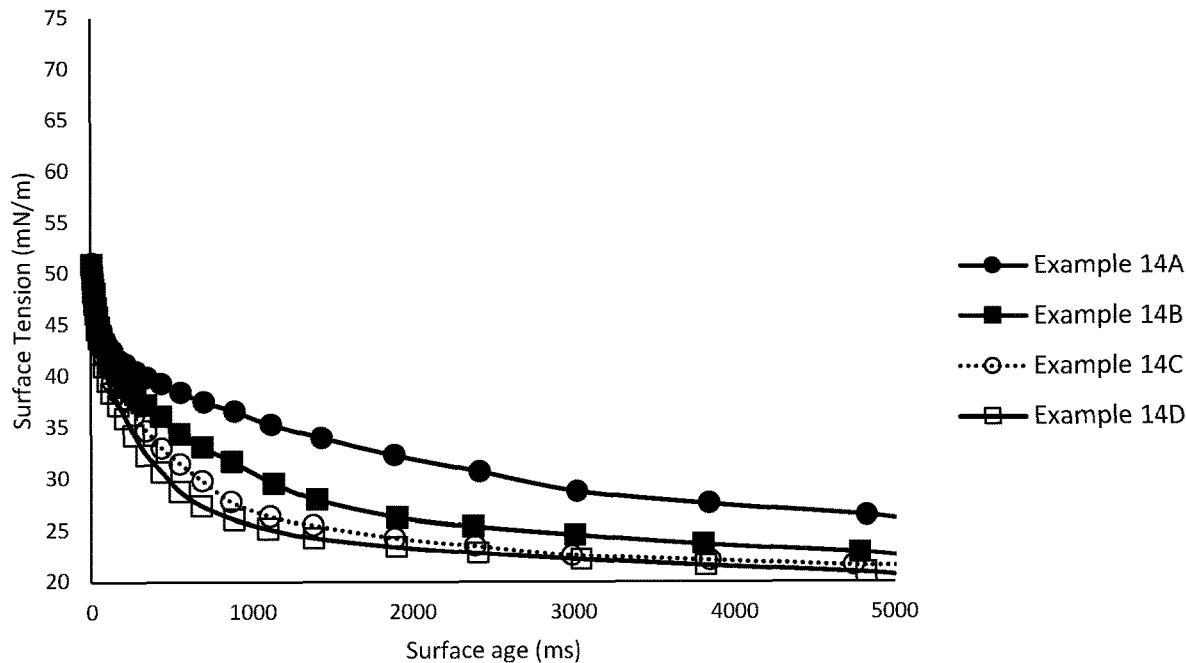
FIG. 10 shows the dynamic surface tension measurements of single-part concentrate embodiments of the present invention based on a short chain fluorosurfactant (Examples 14A-14D) over a range of surface ages FIG. 11 the dynamic surface tension measurements of single-part concentrate embodiments of the present invention based on a branched alkyl alkoxylate (Examples 15A-15G) over a range of surface ages.

FIG. 10 shows a plot of surface tension in mN/m vs surface age (in milliseconds), and Table 25 shows the surface tension at selected surface ages. As can be seen, these formulations provide for a rapid drop in surface tension with very short surface ages.

TABLE 25

|  | Dynamic Surface tension (mN/m) | | | |
| --- | --- | --- | --- | --- |
| Surface age (ms) | 14-A | 14-B | 14-C | 14-D |
| 250 | 41 | 39 | 37 | 35 |
| 500 | 39 | 35 | 32 | 30 |
| 5000 | 26 | 23 | 22 | 21 |

Example 15

The following examples of single-part disinfectant concentrates are based on the use of Bayhibit AM as a corrosion inhibitor, with Ecosurf LFE-635 as the fast wetting surfactant.

The formulations as shown in Table 26 were prepared, using either Triton H66 or Pluronic PE6400 as the solubilising agent.

TABLE 26

|  | Composition (% w/w) | | | | | | |
| --- | --- | --- | --- | --- | --- | --- | --- |
|  | 15-A | 15-B | 15-C | 15-D | 15-E | 15-F | 15-G |
| Proxitane | 91.74 | 90.14 | 95.24 | 94.34 | 92.59 | 92.17 | 91.74 |
| Pluronic PE6400 | 0.00 | 0.00 | 4.76 | 4.72 | 4.63 | 4.61 | 4.59 |
| Ecosurf LFE-635 | 2.75 | 4.50 | 0.00 | 0.94 | 1.85 | 2.30 | 2.75 |
| Bayhibit AM | 0.92 | 0.89 | 0.00 | 0.00 | 0.93 | 0.92 | 0.92 |
| Triton H66 | 4.59 | 4.47 | 0.00 | 0.00 | 0.00 | 0.00 | 0.00 |

2 ml of each formulation were pipetted into 100 ml volumetric flasks containing ca 80 ml tap water. The solutions were then made up to the mark with additional tap water to form the working disinfectant solutions. The approximate functional compositions of the working solutions are shown in Table 27.

TABLE 27

|  | 15-A | 15-B | 15-C | 15-D | 15-E | 15-F | 15-G |
| --- | --- | --- | --- | --- | --- | --- | --- |
| Corrosion inhibitor | 0.018 | 0.018 | 0.000 | 0.000 | 0.019 | 0.018 | 0.018 |
| Surfactant | 0.055 | 0.090 | 0.095 | 0.113 | 0.130 | 0.138 | 0.147 |
| Hydrotrope | 0.092 | 0.089 | 0.000 | 0.000 | 0.000 | 0.000 | 0.000 |
| PAA | 0.092 | 0.090 | 0.095 | 0.094 | 0.093 | 0.092 | 0.092 |

The dynamic surface tensions of the working disinfectant solutions were then measured as described in Example 3.

Figure 11:
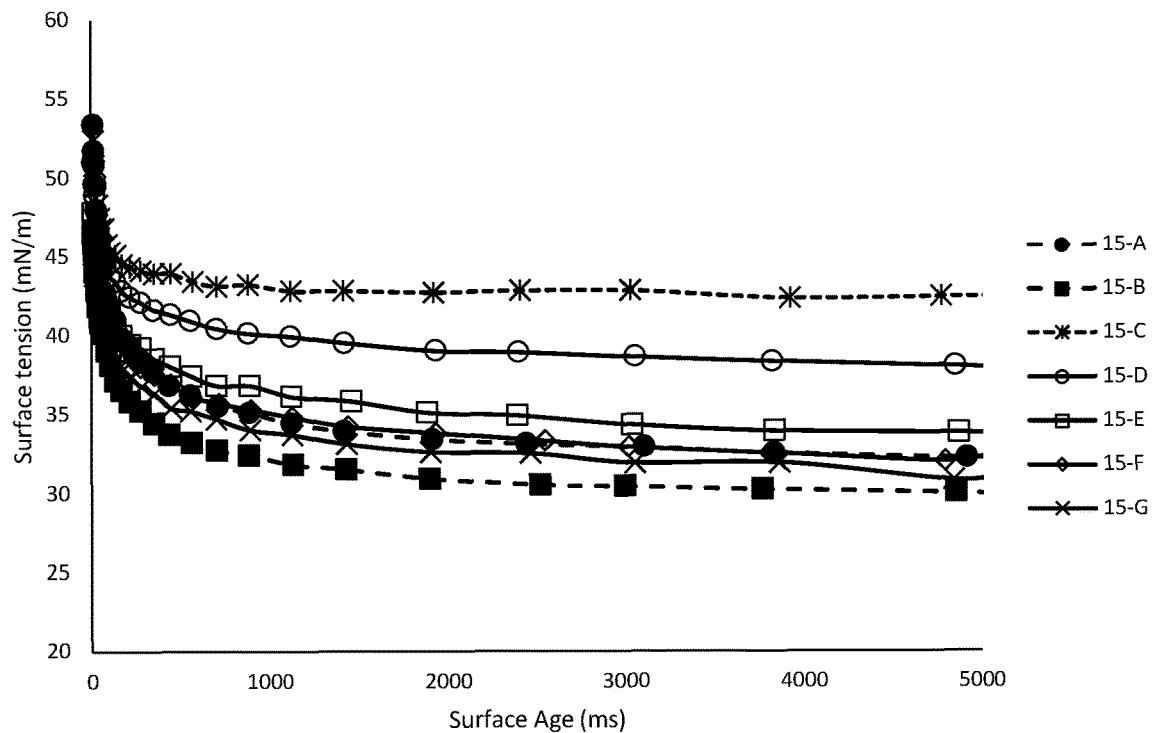

FIG. 11 shows a plot of surface tension in mN/m vs surface age (in milliseconds), and Table 28 shows the surface tension at selected surface ages. Again, these formulations provide for a rapid drop in surface tension with very short surface ages.

TABLE 28

|  | Dynamic surface tension (mN/m) | | | | | | |
| --- | --- | --- | --- | --- | --- | --- | --- |
| Surface age (ms) | 15-A | 15-B | 15-C | 15-D | 15-E | 15-F | 15-G |
| 250 | 38.8 | 35.5 | 44.2 | 42.2 | 39.3 | 38.0 | 37.1 |
| 500 | 36.5 | 33.5 | 43.7 | 41.1 | 37.7 | 36.5 | 35.3 |
| 5000 | 32.2 | 29.9 | 42.4 | 37.9 | 33.7 | 32.3 | 30.9 |

Of note here is that whilst a formulation containing just Proxitane and Pluronic PE6400 (example 15C) shows a rapid initial drop in surface tension, there is only a slight drop from the value of 43.7 mN/m at 500 ms to the value of 42.4 mN/m at 5000 ms. The addition of the branched alkyl alkoxylate Ecosurf LFE-635 demonstrates a significant improvement in surface tension reduction, particularly when present in the formulation concentrate at levels greater than 1.85% w/w. As may be seen in Table 28, formulations containing greater than 1.85% w/w Ecosurf FFE-635 all gave surface tensions of less than 40 mN/m at surface ages in excess of 250 ms.

Example 17: Microbiological Efficacy

The following working disinfectant solutions were prepared as follows:

Test Disinfectant 1

2 ml of Example 10 was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 857 ppm PAA and 3901 ppm of hydrogen peroxide.

Test Disinfectant 2 (Control Formulation)

2 ml of Rapicide PA Part B was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 857 ppm PAA and 3929 ppm of hydrogen peroxide.

Both working disinfectant solutions were then assessed for sporicidal efficacy in a time-kill study using a suspension of *Bacillus subtilis* spores (ATCC 19659) containing $1.8 \times 10^8$ CFU/ml with 5% horse serum added as an organic soil.

Testing was performed at 40° C., using a range of contact times (5 sec, 60 sec, 120 sec, 180 sec and 240 sec, using 5 replicates per time point. After the requisite contact time, the disinfectant was neutralised, and the surviving spores enumerated.

As can be seen in Table 29, Test solution 1, prepared using the formulation of Example 10 demonstrated a 6 $\log_{10}$ reduction

TABLE 29

| | | Log reductions ($\log_{10}$) | | | | |
|---|---|---|---|---|---|---|
| Test solution | Concentrations | 5 sec | 60 sec | 120 sec | 180 sec | 240 sec |
| Test solution 1 (Example 10) | PAA-857 ppm HP-3901 ppm | 1.49 | 6.05 | >7.23 | >7.23 | >7.23 |
| Test solution 2 (control) | PAA-857 ppm HP-3929 ppm | 1.37 | 3.21 | 5.69 | 7.16 | >7.23 |
| Inoculum control | | | $1.7 \times 10^8$ (8.23 $\log_{10}$) | | | |

Example 16: Microbiological Efficacy: Spore Carrier Test

In this test a screening carrier test based on the AOAC sporicidal activity test, using 4 carriers per test substance at two concentrations was performed.

Test Disinfectant 1

2 ml of the formulation of Example 10 was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 856 ppm PAA and 3840 ppm of hydrogen peroxide (HP).

Four porcelain penicylinders, inoculated with *Bacillus subtilis* spores under dirty conditions (5% horse serum) were then treated with the working disinfectant solution at 40° C. for a range of time points (60 seconds, 120 seconds, 180 seconds and 240 seconds). The disinfectant was neutralised with 10 ml of a T6 neutraliser and the samples incubated to assess growth/no growth to determine any residual viable spores.

Test Disinfectant 2 (Control)

2 ml of Rapicide PA Part B was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 868 ppm PAA and 4000 ppm of hydrogen peroxide.

Four porcelain penicylinders, inoculated with *Bacillus subtilis* spores under dirty conditions (5% horse serum) were then treated with the disinfectant solution at 40° C. for a range of time points (60 seconds, 120 seconds, 180 seconds and 240 seconds). The disinfectant was neutralised with 10 ml of a T6 neutraliser and the samples incubated to assess growth/no growth to determine any residual viable spores.

After incubation, the following results were obtained. As can be seen from Table 30, whilst the test substance (Example 10) showed no growth at all time points, the control sample (Example 6, Rapicide PA) did show survivors at 60 seconds and 120 seconds. It is noted that this PAA concentration is that indicated for high-level disinfection for Rapicide PA, whereas the temperature is that stated for sterilisation with Rapicide PA (albeit the sterilisation time is typically 10 minutes).

TABLE 30

| | | Carriers with growth/no growth | | | |
|---|---|---|---|---|---|
| Sample | Concentrations | 60 sec | 120 sec | 180 sec | 240 sec |
| Test solution 1 (Example 10) | PAA - 856 ppm HP - 3840 ppm | 0/4 | 0/4 | 0/4 | 0/4 |
| Test solution 2 (control) | PAA - 868 ppm HP - 4000 ppm | 2/4 | 1/4 | 0/4 | 0/4 |
| Inoculum control (spores/carrier) | | $2.91 \times 10^6$ (6.46 $\log_{10}$) | | | |

Example 17: Microbiological Efficacy: Spore Carrier Test (Higher PAA Concentration)

In this test a screening carrier test based on the AOAC sporicidal activity test, but again using 4 carriers per test substance at two concentrations was performed.

Test Disinfectant 1

2 ml of the formulation of Example 10 was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 1700 ppm PAA and 7821 ppm of hydrogen peroxide.

Four porcelain penicylinders, inoculated with *Bacillus subtilis* spores under dirty conditions (5% horse serum) were then treated with the working disinfectant solution at 40° C. for a range of time points (60 seconds, 120 seconds, 180 seconds and 240 seconds). The disinfectant was neutralised with 10 ml of a T6 neutraliser and the samples incubated to assess growth/no growth to determine any residual viable spores.

Test Disinfectant 2 (Control)

2 ml of Rapicide PA Part B was pipetted into a 100 ml volumetric flask containing approximately 80 ml of artificial hard water (340 mg/L as CaCO3), along with 2 ml of a 5% PAA solution (Rapicide PA Part A). The solution was made up to the mark with additional hard water. The resultant working disinfectant solution was then titrated to determine its PAA content, and then diluted further with hard water to give a final PAA content of 1706 ppm PAA and 8019 ppm of hydrogen peroxide.

4 porcelain penicylinders, inoculated with *Bacillus subtilis* spores under dirty conditions (5% horse serum) were then treated with the working disinfectant solution at 40° C. for a range of time points (60 seconds, 120 seconds, 180 seconds and 240 seconds). The disinfectant was neutralised and the samples incubated to assess growth/no growth to determine any residual viable spores After incubation, the following results were obtained. As can be seen from Table 31, whilst the test substance (Example 10) showed no growth at all time points, the control sample (Example 6, Rapicide PA) did show survivors at 60 seconds.

TABLE 31

| Sample | Concentrations | Carriers with growth/no growth | | | |
|---|---|---|---|---|---|
| | | 60 sec | 120 sec | 180 sec | 240 sec |
| Test solution 1 (Example 10) | PAA - 1700 ppm HP - 7821 ppm | 0/4 | 0/4 | 0/4 | 0/4 |
| Test solution 2 (control) | PAA - 1706 ppm HP - 8019 ppm | 1/4 | 0/4 | 0/4 | 0/4 |
| Inoculum control (spores/carrier) | | 2.91 × 10$^6$ (6.46 log$_{10}$) | | | |

The invention claimed is:

1. A working disinfectant solution for the sterilization or disinfection of a medical device providing at least a 6 log$_{10}$ reduction in both bacteria and spores, wherein said solution comprises an aqueous dilution of a disinfectant concentrate, comprising:
   (a) peracetic acid;
   (b) at least one non-ionic surfactant; and
   (c) at least one corrosion inhibitor,
   wherein said working disinfectant solution exhibits a dynamic surface tension less than about 50 mN/m at a surface age of 250 ms, and less than about 46 mN/m at a surface age of 500 ms, when measured by the Maximum Bubble Pressure method at 20-25° C.;
   wherein the at least one non-ionic surfactant is selected from the group consisting of block copolymers of polyethylene oxide and polypropylene oxide, ethoxylated propoxylated 2-ethyl-1-hexanol, and combinations thereof and the concentration of the at least one non-ionic surfactant is about 0.05% w/v to about 0.5% w/v (about 500 ppm to about 5000 ppm) of the working disinfectant solution; and
   wherein the at least one corrosion inhibitor is selected from the group consisting of benzotriazole, alkali metal phosphates, alkali metal nitrate salts, alkali metal nitrite salts, 2-phosphonobutane-1,2,4-tricarboxylic acid salts, metal molybdate salts and combinations thereof.

2. A working disinfectant solution according to claim 1 wherein the peracetic acid concentration is between 0.01% w/v to about 1.0% w/v (about 100 ppm to about 10,000 ppm) of the working disinfectant solution.

3. A working disinfectant solution according to claim 2 wherein the peracetic acid concentration is between about 0.02% w/v to about 0.5% w/v (about 200 ppm to about 5000 ppm) of the working disinfectant solution.

4. A working disinfectant solution according to claim 1 wherein the disinfectant concentrate comprises between about 0.1% w/w and about 20% w/w peracetic acid of the disinfectant concentrate.

5. A working disinfectant solution according to claim 4 wherein the disinfectant concentrate comprises between about 1% w/w and about 15% w/w peracetic acid of the disinfectant concentrate.

6. A working disinfectant solution according to claim 5 wherein the disinfectant concentrate comprises between about 4% w/w and about 6% w/w peracetic acid of the disinfectant concentrate.

7. A working disinfectant solution according to claim 1 wherein the disinfectant concentrate further comprises at least one hydrotrope.

8. A working disinfectant solution according to claim 7 wherein the at least one hydrotrope is selected from the group consisting of potassium naphthalene sulfonate, potassium cresylphosphate, potassium octyliminodipropionate, sodium naphthalene sulfonate, sodium cresyl phosphate, sodium octyliminodipropionate, pentyl glucoside, hexyl glucoside, octyl glucoside, isooctyl glucoside, and mixtures thereof.

9. A method of disinfecting or sterilizing a medical device providing at least a 6 log$_{10}$ reduction in both bacteria and spores, which method comprises contacting said medical device with a working disinfectant solution comprising an aqueous dilution of a disinfectant concentrate, comprising:
   (a) peracetic acid;
   (b) at least one non-ionic surfactant; and
   (c) at least one corrosion inhibitor,
   wherein said working disinfectant solution exhibits a dynamic surface tension less than about 50 mN/m at a surface age of 250 ms, and less than about 46 mN/m at a surface age of 500 ms when measured by the Maximum Bubble Pressure method at 20-25° C.;
   wherein the at least one non-ionic surfactant is selected from the group consisting of block copolymers of polyethylene oxide and polypropylene oxide, ethoxylated propoxylated 2-ethyl-1-hexanol, and combinations thereof and the concentration of the at least one non-ionic surfactant is about 0.05% w/v to about 0.5% w/v (about 500 ppm to about 5000 ppm) of the working disinfectant solution; and
   wherein the at least one corrosion inhibitor is selected from the group consisting of benzotriazole, alkali metal phosphates, alkali metal nitrate salts, alkali metal nitrite salts, 2-phosphonobutane-1,2,4-tricarboxylic acid salts, metal molybdate salts and combinations thereof.

10. The method according to claim 9 wherein the disinfectant concentrate comprises between about 1% w/w and about 15% w/w peracetic acid of the disinfectant concentrate.

11. The method according to claim 10 wherein the disinfectant concentrate comprises between about 4% w/w and about 6% w/w peracetic acid of the disinfectant concentrate.

12. The method according to claim 9 wherein the disinfectant concentrate further comprises at least one hydrotrope.

13. The method according to claim 12 wherein the at least one hydrotrope is selected from the group consisting of potassium naphthalene sulfonate, potassium cresylphosphate, potassium octyliminodipropionate, sodium naphthalene sulfonate, sodium cresyl phosphate, sodium octyliminodipropionate, pentyl glucoside, hexyl glucoside, octyl glucoside, isooctyl glucoside, and mixtures thereof.

\* \* \* \* \*